(12) United States Patent
Noel

(10) Patent No.: US 11,759,491 B2
(45) Date of Patent: Sep. 19, 2023

(54) SOLVENTS, METHODS, AND SYSTEMS FOR ISOLATING BOTANICAL EXTRACTS FROM PLANTS

(71) Applicant: Armand J. Noel, Tempe, AZ (US)

(72) Inventor: Armand J. Noel, Tempe, AZ (US)

(73) Assignee: Super Critical IP, LLC, Phoenix, AZ (US)

( * ) Notice: Subject to any disclaimer, the term of this patent is extended or adjusted under 35 U.S.C. 154(b) by 0 days.

(21) Appl. No.: 17/813,706

(22) Filed: Jul. 20, 2022

(65) Prior Publication Data

US 2023/0036925 A1 Feb. 2, 2023

Related U.S. Application Data

(60) Provisional application No. 63/227,875, filed on Jul. 30, 2021, provisional application No. 63/227,542, filed on Jul. 30, 2021.

(51) Int. Cl.

| | | |
|---|---|---|
| C07C 37/00 | (2006.01) |
| C07C 37/84 | (2006.01) |
| A61K 31/00 | (2006.01) |
| A61K 36/28 | (2006.01) |
| A61K 36/185 | (2006.01) |
| A61K 31/05 | (2006.01) |
| A61K 31/352 | (2006.01) |
| C07C 37/74 | (2006.01) |
| C07D 311/80 | (2006.01) |

(52) U.S. Cl.
CPC .............. *A61K 36/28* (2013.01); *A61K 31/05* (2013.01); *A61K 31/352* (2013.01); *A61K 36/185* (2013.01); *C07C 37/003* (2013.01); *C07C 37/74* (2013.01); *C07C 37/84* (2013.01); *C07D 311/80* (2013.01); *A61K 2236/35* (2013.01); *A61K 2236/37* (2013.01); *A61K 2236/51* (2013.01); *A61K 2236/53* (2013.01); *C07B 2200/13* (2013.01); *C07C 2601/16* (2017.05)

(58) Field of Classification Search
CPC ....... C07C 37/003; C07C 37/74; C07C 37/84; C07B 2200/13; A61K 31/658
See application file for complete search history.

(56) References Cited

U.S. PATENT DOCUMENTS

2020/0255389 A1 8/2020 Tegen et al.
2021/0189444 A1 6/2021 Alviar et al.

FOREIGN PATENT DOCUMENTS

WO 202048077 12/2020

*Primary Examiner* — Sikarl A Witherspoon
(74) *Attorney, Agent, or Firm* — Spencer Fane LLP

(57) ABSTRACT

The present invention provides improved solvents, methods, and systems for isolating purified cannabinoids from various sources. It has been found that $C_9$ to $C_{11}$ non-aromatic hydrocarbon solvents, and especially n-decane, work surprisingly well for crystallization of cannabinoids such as cannabidiol. Some variations provide a method of isolating cannabinoids from a cannabinoid-containing solution, comprising contacting the solution with a $C_9$-$C_{11}$ non-aromatic hydrocarbon solvent (e.g., n-decane) at a first temperature, to generate a mixture; cooling the mixture to precipitate cannabinoids; and isolating the precipitated cannabinoids. Other variations provide a method of isolating cannabinoids from a cannabinoid-containing solution, comprising contacting the solution with a $C_9$-$C_{11}$ non-aromatic hydrocarbon solvent (e.g., n-decane) at a first temperature below the solvent boiling point, to generate a mixture; subjecting the mixture to a second temperature that causes vaporization of the solvent, to precipitate at least some of the cannabinoids; and isolating the precipitated cannabinoids.

72 Claims, 9 Drawing Sheets

| COMPOUND | LOD/LOQ (mg/g) | MEASUREMENT UNCERTAINTY (mg/g) | RESULT (mg/g) | RESULT (%) |
|---|---|---|---|---|
| CBD | 0.004 / 0.011 | ±3.9563 | 82.594 | 8.2594 |
| CBG | 0.002 / 0.005 | ±0.2427 | 3.902 | 0.3902 |
| CBDV | 0.002 / 0.007 | ±0.0160 | 0.306 | 0.0306 |
| Δ9THC | 0.002 / 0.005 | ±0.0105 | 0.149 | 0.0149 |
| CBC | 0.003 / 0.010 | ±0.0040 | 0.097 | 0.0097 |
| CBL | 0.003 / 0.008 | ±0.0010 | 0.021 | 0.0021 |
| CBN | 0.001 / 0.004 | ±0.0003 | 0.008 | 0.0008 |
| Δ8THC | 0.01 / 0.02 | N/A | ND | ND |
| THCa | 0.001 / 0.002 | N/A | ND | ND |
| THCV | 0.002 / 0.008 | N/A | ND | ND |
| THCVa | 0.002 / 0.005 | N/A | ND | ND |
| CBDa | 0.001 / 0.003 | N/A | ND | ND |
| CBDVa | 0.001 / 0.003 | N/A | ND | ND |
| CBGa | 0.002 / 0.006 | N/A | ND | ND |
| CBCa | 0.001 / 0.004 | N/A | ND | ND |
| SUM OF CANNABINOIDS | | | 87.077 mg/g | 8.7077% |

FIG. 9

SOLVENTS, METHODS, AND SYSTEMS FOR ISOLATING BOTANICAL EXTRACTS FROM PLANTS

PRIORITY DATA

This U.S. non-provisional patent application claims priority to U.S. Provisional Patent App. No. 63/227,542, filed on Jul. 30, 2021, and to U.S. Provisional Patent App. No. 63/227,875, filed on Jul. 30, 2021, each of which is hereby incorporated by reference herein.

FIELD OF THE INVENTION

The present invention generally relates to methods and systems for isolating cannabinoids from plants or plant extracts, or from synthetic pathways, and cannabinoid compositions obtained therefrom. The present invention also relates to methods and systems for isolating various botanical extracts from plants.

BACKGROUND OF THE INVENTION

Biomass extracts have been used as a source of medicine throughout history and continue to serve as the basis for many pharmaceuticals, cosmeceuticals, and nutraceuticals today. Valuable biomass extracts include, but are by no means limited to, hemp, hops, chamomile, dandelion, *echinacea*, marigold, lavender, and many other therapeutic plants and herbs.

Cannabinoids are compounds found in the *Cannabis* plant. The *Cannabis* plant has been used for both medical and recreational purposes since prehistoric times, and is finding increasing scientific interest and acceptance for applications in modern medicine. *Cannabis sativa* and *Cannabis* indica are the species most often utilized.

The *Cannabis* plant contains hundreds of individual compounds, including over 100 cannabinoids. Notable cannabinoids include tetrahydrocannabinol (THC) and cannabidiol (CBD) which are commonly extracted from the *Cannabis* plant on a commercial basis. *Cannabis* indica tends to produce higher CBD/THC ratios, compared to *Cannabis sativa*, unless the *Cannabis sativa* strain is cultivated to reduce THC.

Hemp, or industrial hemp, is a plant variety of the *Cannabis sativa* species that is grown specifically for industrial use. Hemp is cultivated to reduce the THC content, which means the CBD/THC ratio is very high. In most cases, manufacturers use the leaves and flowers of the hemp plant to make CBD products. CBD is not psychoactive and is a proven pharmaceutical to treat seizure. At present, clinical research on CBD includes studies related to pain, anxiety, cognition, movement disorders, and many other conditions.

Compound isolation is an important process during the clean-up or production of certain compounds. Many chemical-engineering unit operations are configured for compound isolation. These processes include crystallization, distillation, chromatography, filtration, and many other. Crystallization is a proven technique to produce high-purity compound mixtures and for this reason crystallization is the foundation for many pharmaceutical processes.

Crystallization is generally the process by which a solid forms, where the atoms or molecules are highly organized into a structure known as a crystal. Some of the ways by which crystals form are precipitating from a solution, freezing, or more rarely deposition directly from a gas.

Compound crystallization via precipitation from solution is dependent on the solubility of the compound in a certain solvent over a broad temperature range. The goal is to choose a solvent for which the compound (the solute) is soluble at high temperatures, but insoluble or at least less soluble at lower temperatures. Initially, the compound is dissolved into the solvent at a high temperature. As the temperature of the solution decreases, the solute becomes oversaturated (higher than equilibrium concentration) and begins to precipitate out of the solution as a solid crystal.

Currently in the hemp/cannabinoid industry, many labs or processors are utilizing crystallization as their final isolation step, to recover a cannabinoid from a cannabinoid distillate or extract. However, the crystallizations are conventionally carried out utilizing highly flammable solvents such as pentane and n-heptane. Not only are these solvents flammable at standard operation conditions, but they require large amounts of energy (e.g., electricity for refrigeration) to effectively crystalize the cannabinoids. Processors first heat the solvents and mix in cannabinoid distillate in preparation for the precipitation. To reduce the solubility of these solvents, processors are forced to bring the mixture temperature down to −10° C. or in some cases −50° C. During this cool-down procedure, large amounts of chilling capacity are necessary, adding much cost. If the low temperature of the mixture is not achieved, then a large amount of cannabinoid will be left in the solvent and unable to crystallization due to the solubility still being quite high at the elevated temperature. This inability to precipitate the cannabinoid out of the solvent leads to decrease yields and increased cost of goods.

In view of the aforementioned needs in the art, improved solvents, methods, and systems are commercially desired for isolating purified cannabinoids from plant extracts or distillates, as well as from synthetic pathways.

SUMMARY OF THE INVENTION

The present invention addresses the aforementioned needs in the art, as will now be summarized and then further described in detail below.

Some variations of the invention provide a method of isolating one or more cannabinoids from a cannabinoid-containing solution, the method comprising contacting the cannabinoid-containing solution with a solvent comprising decane at a first temperature, to generate a mixture; cooling the mixture to reach a second temperature that is lower than the first temperature, to precipitate at least some of the cannabinoids as precipitated cannabinoids; and isolating the precipitated cannabinoids from the mixture.

In some embodiments, the cannabinoid-containing solution is obtained from a process of extracting cannabinoids from a plant material, wherein that process is optionally co-located with a site at which the method is conducted. In other embodiments, the cannabinoid-containing solution is obtained from an external source. In certain embodiments, the cannabinoid-containing solution is obtained from multiple sources, such as a combination of a co-located process and an external source. In some embodiments, the cannabinoid-containing solution contains cannabinoids from a synthetic pathway.

The precipitated cannabinoids may be selected from the group consisting of cannabidiol, cannabidiolic acid, cannabinol, cannabigerol, cannabichromene, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof. In certain embodiments, the precipitated cannabinoids include cannabidiol. The cannabidiol may be at least 50 wt % or at least 90 wt %, for example, of total cannabinoid compounds contain in the precipitated cannabinoids.

In this disclosure, unless otherwise stated, "decane" ($C_{10}H_{22}$) includes not only n-decane but also any one or more of its 74 isomers. In some embodiments, the decane is linear normal decane ("n-decane"). In some embodiments, the decane is a branched decane. A combination of multiple decane isomers may be utilized.

In some methods, the first temperature is selected from about 20° C. to about 170° C., such as from about 30° C. to about 100° C. In some methods, the second temperature is selected from about −20° C. to about 150° C., such as from about −10° C. to about 100° C., or from about 0° C. to about 50° C. In some embodiments, the temperature difference between the first temperature and the second temperature is from about 10° C. to about 200° C., such as from about 20° C. to about 100° C.

In some methods, the isolating utilizes filtration, centrifugation, evaporation, chromatography, or a combination thereof.

The cannabinoid yield may be at least 75%, calculated as mass of the precipitated cannabinoids, as a percentage of total mass of the cannabinoids in the cannabinoid-containing solution. In some embodiments, the cannabinoid yield is at least 80%, at least 85%, at least 90%, or at least 95%.

Other variations of the invention provide a method of isolating one or more cannabinoids from a cannabinoid-containing solution, the method comprising contacting the cannabinoid-containing solution with a $C_9$-$C_{11}$ non-aromatic hydrocarbon solvent at a first temperature, to generate a mixture; cooling the mixture to reach a second temperature that is lower than the first temperature, to precipitate at least some of the cannabinoids as precipitated cannabinoids; and isolating the precipitated cannabinoids from the mixture.

The cannabinoid-containing solution may be obtained from an external source. Alternatively, or additionally, the cannabinoid-containing solution may be obtained from a process of extracting cannabinoids from a plant material, wherein the process may be co-located with a site at which the method is conducted. In some embodiments, the cannabinoid-containing solution contains cannabinoids from a synthetic pathway.

The precipitated cannabinoids may be selected from the group consisting of cannabidiol, cannabidiolic acid, cannabinol, cannabigerol, cannabichromene, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof.

When the precipitated cannabinoids include cannabidiol, such cannabidiol may be at least 50 wt % of total cannabinoid compounds contain in the precipitated cannabinoids. In some embodiments, the cannabidiol is at least 90 wt % of total cannabinoid compounds contain in the precipitated cannabinoids.

In some embodiments, the $C_9$-$C_{11}$ non-aromatic hydrocarbon solvent is a $C_{10}$ linear, cyclic, or branched alkane solvent. Linear or branched $C_{10}$ alkanes generally have the formula $C_{10}H_{22}$, while cyclic $C_{10}$ alkanes have less hydrogen (e.g., cyclodecane is $C_{10}H_{20}$).

In preferred embodiments, the $C_9$-$C_{11}$ non-aromatic hydrocarbon solvent is selected from the group consisting of n-decane, 2-methylnonane, 3-methylnonane, 4-methylnonane, 5-methylnonane, 3-ethyloctane, 4-ethyloctane, 2,2-dimethyloctane, 2,3-dimethyloctane, 2,4-dimethyloctane, 2,5-dimethyloctane, 2,6-dimethyloctane, 2,7-dimethyloctane, 3,3-dimethyloctane, 3,4-dimethyloctane, 3,5-dimethyloctane, 3,6-dimethyloctane, 4,4-dimethyloctane, 4,5-dimethyloctane, 4-propylheptane, 4-isopropylheptane, 2-methyl-3-ethylheptane, 2-methyl-4-ethylheptane, 2-methyl-5-ethylheptane, 3-methyl-3-ethylheptane, 3-methyl-4-ethylheptane, 3-methyl-5-ethylheptane, 4-methyl-3-ethylheptane, 4-methyl-4-ethylheptane, 2,2,3-trimethylheptane, 2,2,4-trimethylheptane, 2,2,5-trimethylheptane, 2,2,6-trimethylheptane, 2,3,3-trimethylheptane, 2,3,4-trimethylheptane, 2,3,5-trimethylheptane, 2,3,6-trimethylheptane, 2,4,4-trimethylheptane, 2,4,5-trimethylheptane, 2,4,6-trimethylheptane, 2,5,5-trimethylheptane, 3,3,4-trimethylheptane, 3,3,5-trimethylheptane, 3,4,4-trimethylheptane, 3,4,5-trimethylheptane, 2-methyl-3-isopropylhexane, 3,3-diethylhexane, 3,4-diethylhexane, 2,2-dimethyl-3-ethylhexane, 2,2-dimethyl-4-ethylhexane, 2,3-dimethyl-3-ethylhexane, 2,3-dimethyl-4-ethylhexane, 2,4-dimethyl-3-ethylhexane, 2,4-dimethyl-4-ethylhexane, 2,5-dimethyl-3-ethylhexane, 3,3-dimethyl-4-ethylhexane, 3,4-dimethyl-3-ethylhexane, 3,4-dimethyl-4-ethylhexane, 2,2,3,3-tetramethylhexane, 2,2,3,4-tetramethylhexane, 2,2,3,5-tetramethylhexane, 2,2,4,4-tetramethylhexane, 2,2,4,5-tetramethylhexane, 2,2,5,5-tetramethylhexane, 2,3,3,4-tetramethylhexane, 2,3,3,5-tetramethylhexane, 2,3,4,4-tetramethylhexane, 2,3,4,5-tetramethylhexane, 3,3,4,4-tetramethylhexane, 2,4-dimethyl-3-isopropylpentane, 2-methyl-3,3-diethylpentane, 2,2,3-trimethyl-3-ethylpentane, 2,2,4-trimethyl-3-ethylpentane, 2,3,4-trimethyl-3-ethylpentane, 2,2,3,3,4-pentamethylpentane, 2,2,3,4,4-pentamethylpentane, and combinations thereof. In certain preferred embodiments, the $C_9$-$C_{11}$ non-aromatic hydrocarbon solvent is specifically n-decane, or is a solvent comprising n-decane.

In some embodiments, the $C_9$-$C_{11}$ non-aromatic hydrocarbon solvent is a $C_{10}$ linear, cyclic, or branched alkene solvent. An alkene contains at least one carbon-carbon double bond, C=C.

In some embodiments, the $C_9$-$C_{11}$ non-aromatic hydrocarbon solvent is a $C_{10}$ linear, cyclic, or branched alkyne solvent. An alkyne contains at least one carbon-carbon triple bond, C≡C.

In some embodiments, the $C_9$-$C_{11}$ non-aromatic hydrocarbon solvent is a $C_9$ linear, cyclic, or branched alkane solvent, a $C_9$ linear, cyclic, or branched alkene solvent, a $C_9$ linear, cyclic, or branched alkyne solvent, or a combination thereof.

In some embodiments, the $C_9$-$C_{11}$ non-aromatic hydrocarbon solvent is a $C_{11}$ linear, cyclic, or branched alkane solvent, a $C_{11}$ linear, cyclic, or branched alkene solvent, a $C_{11}$ linear, cyclic, or branched alkyne solvent, or a combination thereof.

The $C_9$-$C_{11}$ non-aromatic hydrocarbon solvent may be a single molecule or a mixture of two or more molecules, such as 2, 3, 4, 5, 6, 7, 8, 9, or more distinct molecules. When there are multiple molecules, they may all be $C_9$, all $C_{10}$, all $C_{11}$, a mix of $C_9$ and $C_{10}$, a mix of $C_{10}$ or $C_{11}$, or a mix of $C_9$, $C_{10}$, and $C_{11}$.

In some methods, the first temperature is selected from about 20° C. to about 170° C., such as from about 30° C. to about 100° C. In some methods, the second temperature is selected from about −20° C. to about 150° C., such as from about −10° C. to about 100° C., or from about 0° C. to about 50° C. The temperature difference between the first temperature and the second temperature may be from about 10° C. to about 200° C., such as from about 20° C. to about 100° C.

In various methods, the isolating step utilizes filtration, centrifugation, evaporation, chromatography, or a combination thereof.

The cannabinoid yield may be at least 75%, calculated as mass of the precipitated cannabinoids, as a percentage of total mass of the cannabinoids in the cannabinoid-containing solution. In some embodiments, the cannabinoid yield is at least 80%, is at least 85%, at least 90%, or at least 95%.

In some variations, the invention provides a method of isolating one or more cannabinoids from a cannabinoid-containing solution, the method comprising contacting the cannabinoid-containing solution with a solvent comprising decane at a first temperature below the decane boiling point, to generate a mixture; subjecting the mixture to a second temperature that causes vaporization of the solvent, to precipitate at least some of the cannabinoids as precipitated cannabinoids; and isolating the precipitated cannabinoids from the mixture.

The cannabinoid-containing solution may be obtained from an external source. Alternatively, or additionally, the cannabinoid-containing solution may be obtained from a process of extracting cannabinoids from a plant material, wherein the process is optionally co-located with a site at which the method is conducted. In some embodiments, the cannabinoid-containing solution contains cannabinoids from a synthetic pathway.

The precipitated cannabinoids may be selected from the group consisting of cannabidiol, cannabidiolic acid, cannabinol, cannabigerol, cannabichromene, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof.

When the precipitated cannabinoids include cannabidiol, such cannabidiol may be at least 50 wt % of total cannabinoid compounds contain in the precipitated cannabinoids. In some embodiments, the cannabidiol is at least 90 wt % of total cannabinoid compounds contain in the precipitated cannabinoids.

In some embodiments, the decane is n-decane. In some embodiments, the decane is a branched decane. A combination of multiple decane isomers may be utilized.

In some methods, the first temperature is selected from about 20° C. to about 170° C., such as from about 30° C. to about 100° C. In some methods, the second temperature is selected from about 25° C. to about 250° C., such as from about 100° C. to about 200° C.

In some methods, the isolating utilizes filtration, centrifugation, evaporation, chromatography, or a combination thereof.

The cannabinoid yield may be at least 75%, calculated as mass of the precipitated cannabinoids, as a percentage of total mass of the cannabinoids in the cannabinoid-containing solution. In some embodiments, the cannabinoid yield is at least 80%, is at least 85%, at least 90%, or at least 95%.

Other variations of the invention provide a method of isolating one or more cannabinoids from a cannabinoid-containing solution, the method comprising contacting the cannabinoid-containing solution with a $C_9$-$C_{11}$ non-aromatic hydrocarbon solvent at a first temperature below the solvent boiling point, to generate a mixture; subjecting the mixture to a second temperature that causes vaporization of the solvent, to precipitate at least some of the cannabinoids as precipitated cannabinoids; and isolating the precipitated cannabinoids from the mixture.

The cannabinoid-containing solution may be obtained from an external source. Alternatively, or additionally, the cannabinoid-containing solution may be obtained from a process of extracting cannabinoids from a plant material, wherein the process may be co-located with a site at which the crystallization method is conducted. In some embodiments, the cannabinoid-containing solution contains cannabinoids from a synthetic pathway.

The precipitated cannabinoids may be selected from the group consisting of cannabidiol, cannabidiolic acid, cannabinol, cannabigerol, cannabichromene, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof.

When the precipitated cannabinoids include cannabidiol, such cannabidiol may be at least 50 wt % of total cannabinoid compounds contain in the precipitated cannabinoids. In some embodiments, the cannabidiol is at least 90 wt % of total cannabinoid compounds contain in the precipitated cannabinoids.

The $C_9$-$C_{11}$ non-aromatic hydrocarbon solvent may be selected from the group consisting of a $C_{10}$ linear, cyclic, or branched alkane solvent; a $C_{10}$ linear, cyclic, or branched alkene solvent; a $C_{10}$ linear, cyclic, or branched alkyne solvent; a $C_9$ linear, cyclic, or branched alkane solvent; a $C_9$ linear, cyclic, or branched alkene solvent; a $C_9$ linear, cyclic, or branched alkyne solvent; a $C_{11}$ linear, cyclic, or branched alkane solvent; a $C_{11}$ linear, cyclic, or branched alkene solvent; a $C_{11}$ linear, cyclic, or branched alkyne solvent; and combinations thereof.

In various methods employing vaporization of a $C_9$-$C_{11}$ non-aromatic hydrocarbon solvent, the first temperature is selected from about 20° C. to about 170° C., such as from about 30° C. to about 100° C.

In various methods employing vaporization of a $C_9$-$C_{11}$ non-aromatic hydrocarbon solvent, the second temperature is selected from about 25° C. to about 250° C., such as from about 100° C. to about 200° C.

In various methods employing vaporization of a $C_9$-$C_{11}$ non-aromatic hydrocarbon solvent, the isolating step utilizes one or more of filtration, centrifugation, evaporation, or chromatography.

The cannabinoid yield may be at least 75%, calculated as mass of the precipitated cannabinoids, as a percentage of total mass of the cannabinoids in the cannabinoid-containing solution. In some embodiments, the cannabinoid yield is at least 80%, at least 85%, at least 90%, or at least 95%.

Variations of the invention provide a process for producing cannabinoids from a cannabinoid-containing plant material, the process comprising:

(a) providing a starting cannabinoid-containing plant material;

(b) exposing the starting cannabinoid-containing plant material to a process solvent, thereby forming a cannabinoid-containing solution containing cannabinoids dissolved and/or suspended in the process solvent;

(c) contacting the cannabinoid-containing solution with a crystallization-inducing solvent comprising decane at a first temperature, to generate a mixture;

(d) cooling the mixture to reach a second temperature that is lower than the first temperature, to precipitate at least some of the cannabinoids as precipitated cannabinoids; and (e) isolating and recovering the precipitated cannabinoids from the mixture.

The cannabinoid-containing plant material may be selected from *Cannabis sativa, Cannabis indica, Cannabis ruderalis, Echinacea purpurea, Echinacea angustifolia, Acmella oleracea, Helichrysum umbraculigerum*, or *Radula marginata*. In typical embodiments, the cannabinoid-containing plant material is selected from *Cannabis* species.

The process solvent may be supercritical carbon dioxide. The process solvent may be a non-polar solvent. The process solvent may be a hydrocarbon, such as a $C_2$-$C_8$ alkane. The process solvent may be a $C_1$-$C_{12}$ alcohol, such as ethanol. In certain embodiments, the process solvent is not n-decane. In certain embodiments, the process solvent is not a $C_{10}$ alkane.

In some embodiments, all process steps are conducted at a single site. In other embodiments, there are at least two different sites across which a process is carried out.

The precipitated cannabinoids may be selected from the group consisting of cannabidiol, cannabidiolic acid, cannabinol, cannabigerol, cannabichromene, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof.

In some embodiments, the precipitated cannabinoids include cannabidiol. The cannabidiol may at least 50 wt %, or at least 90 wt %, of total cannabinoid compounds contain in the precipitated cannabinoids, for example.

The crystallization-inducing solvent in step (c) is preferably different than the process solvent in step (b). In some embodiments, the crystallization-inducing solvent is or includes n-decane. In some embodiments, the crystallization-inducing solvent is or includes branched decane(s). The process solvent may be removed, at least in part, prior to step (c).

The first temperature in step (c) may be selected from about 20° C. to about 170° C., such as from about 30° C. to about 100° C. The second temperature in step (d) may be selected from about −20° C. to about 150° C., such as from about −10° C. to about 100° C., or from about 0° C. to about 50° C. The temperature difference between the first temperature and the second temperature may be from about 10° C. to about 200° C., such as from about 20° C. to about 100° C.

The isolating in step (e) may utilize one or more of filtration, centrifugation, evaporation, distillation, or chromatography.

In various processes, the cannabinoid yield is at least 75%, calculated as mass of the precipitated cannabinoids, as a percentage of total mass of the cannabinoids in the cannabinoid-containing solution formed in step (b). In some processes, the cannabinoid yield is at least 80%, at least 85%, at least 90%, or at least 95%.

An overall process cannabinoid yield can also be calculated as mass of the precipitated cannabinoids, as a percentage of total mass of the cannabinoids contained in the starting cannabinoid-containing plant material provided in step (a). The overall process cannabinoid yield may be at least 50%, at least 60%, at least 70%, at least 80%, or at least 90%, for example.

The process is preferably continuous or semi-continuous. It is also possible to conduct the process batchwise, or a combination of batch and continuous steps.

The present invention also provides a product comprising the precipitated cannabinoids produced by a method or a process as disclosed.

The present invention also provides a system configured for producing precipitated cannabinoids, the system configured for carrying out a method or a process as disclosed.

Other variations are premised on the isolation of botanical extracts beyond cannabinoids.

Some variations provide a method of isolating a botanical extract from a solution containing the botanical extract, the method comprising contacting the solution with a $C_9$-$C_{11}$ non-aromatic hydrocarbon solvent at a first temperature, to generate a mixture; cooling the mixture to reach a second temperature that is lower than the first temperature, to precipitate at least some of the botanical extract as a precipitated botanical extract; and isolating the precipitated botanical extract from the mixture.

In various embodiments, the botanical extract is selected from the group consisting of alpha acids, beta acids, herbal extracts, essential oils, flavonoids, alkaloids, cannabinoids, and combinations thereof.

The $C_9$-$C_{11}$ non-aromatic hydrocarbon solvent may be a $C_{10}$ linear, cyclic, or branched alkane solvent. In certain preferred embodiments, the $C_{10}$ linear, cyclic, or branched alkane solvent is n-decane.

The $C_9$-$C_{11}$ non-aromatic hydrocarbon solvent may be a $C_{10}$ linear, cyclic, or branched alkene solvent or a $C_{10}$ linear, cyclic, or branched alkyne solvent.

The $C_9$-$C_{11}$ non-aromatic hydrocarbon solvent may be a $C_9$ linear, cyclic, or branched alkane solvent or a $C_{11}$ linear, cyclic, or branched alkane solvent.

In some embodiments, the first temperature is selected from about 20° C. to about 170° C. In certain embodiments, the first temperature is selected from about 30° C. to about 100° C.

In some embodiments, the second temperature is selected from about −20° C. to about 150° C., for example. In certain embodiments, the second temperature is selected from about −10° C. to about 100° C., or from about 0° C. to about 50° C.

In some embodiments, the temperature difference between the first temperature and the second temperature is from about 10° C. to about 200° C. In certain embodiments, the temperature difference is from about 20° C. to about 100° C.

The step of isolating the precipitated botanical extract from the mixture may utilize filtration, centrifugation, evaporation, distillation, chromatography, or a combination thereof.

In some embodiments, the botanical extract yield is at least 75%, calculated as mass of the precipitated botanical extract, as a percentage of total mass of the botanical extract in the solution. In certain embodiments, the botanical extract yield is at least 80%, at least 85%, at least 90%, or at least 95%.

In some methods, the solution is obtained from a process of extracting the botanical extract from a plant material, wherein the process is optionally co-located with a site at which the method is conducted. In other embodiments, the solution containing the botanical extract is provided from an external source.

Other variations relating to isolation of botanical extracts provide a method of isolating a botanical extract from a solution containing the botanical extract, the method comprising contacting the solution with a $C_9$-$C_{11}$ non-aromatic hydrocarbon solvent at a first temperature below the solvent boiling point, to generate a mixture; subjecting the mixture to a second temperature that causes vaporization of the solvent, to precipitate at least some of the botanical extract as a precipitated botanical extract; and isolating the precipitated botanical extract from the mixture.

The botanical extract may be selected from the group consisting of alpha acids, beta acids, herbal extracts, essential oils, flavonoids, alkaloids, cannabinoids, and combinations thereof, for example.

In some embodiments, the $C_9$-$C_{11}$ non-aromatic hydrocarbon solvent is a $C_{10}$ linear, cyclic, or branched alkane solvent, such as (but not limited to) n-decane.

In some embodiments, the $C_9$-$C_{11}$ non-aromatic hydrocarbon solvent is a $C_{10}$ linear, cyclic, or branched alkene solvent or a $C_{10}$ linear, cyclic, or branched alkyne solvent.

In some embodiments, the $C_9$-$C_{11}$ non-aromatic hydrocarbon solvent is a $C_9$ linear, cyclic, or branched alkane solvent.

In some embodiments, the $C_9$-$C_{11}$ non-aromatic hydrocarbon solvent is a $C_{11}$ linear, cyclic, or branched alkane solvent.

In some embodiments, the first temperature is selected from about 20° C. to about 170° C. In certain embodiments, the first temperature is selected from about 30° C. to about 100° C.

In some embodiments, the second temperature is selected from about 25° C. to about 250° C. In certain embodiments, the second temperature is selected from about 100° C. to about 200° C.

The step of isolating the precipitated botanical extract from the mixture may utilize filtration, centrifugation, evaporation, distillation, chromatography, or a combination thereof.

In some methods, the botanical extract yield is at least 75%, calculated as mass of the precipitated botanical extract, as a percentage of total mass of the botanical extract in the solution. The botanical extract yield may be at least 80%, at least 85%, at least 90%, or at least 95%, in various embodiments.

The solution containing the botanical extract may be obtained from a process of extracting the botanical extract from a plant material. That process may be co-located with a site at which the method is conducted. In other embodiments, the solution containing the botanical extract is provided from an external source.

Still other variations provide a process for producing a botanical extract from a plant material, the process comprising:

(a) providing a starting plant material;

(b) exposing the starting plant material to a process solvent, thereby forming a solution containing a botanical extract dissolved and/or suspended in the process solvent;

(c) contacting the solution with a crystallization-inducing solvent comprising a $C_9$-$C_{11}$ non-aromatic hydrocarbon solvent at a first temperature, to generate a mixture;

(d) cooling the mixture to reach a second temperature that is lower than the first temperature, to precipitate at least some of the botanical extract as a precipitated botanical extract; and (e) isolating and recovering the precipitated botanical extract from the mixture.

The botanical extract may be selected from the group consisting of alpha acids, beta acids, herbal extracts, essential oils, flavonoids, alkaloids, cannabinoids, and combinations thereof. Other botanical extracts may be isolated and recovered as well, depending on the starting plant material.

In some processes, the process solvent is supercritical carbon dioxide. In some processes, the process solvent is a non-polar solvent. In certain processes, the process solvent is a hydrocarbon, such as a $C_2$-$C_{12}$ alkane (e.g., a $C_9$-$C_{11}$ alkane, such as n-decane). In some processes, the process solvent is not n-decane. In some processes, the process solvent is a $C_1$-$C_{12}$ alcohol.

Within the crystallization-inducing solvent, the $C_9$-$C_{11}$ non-aromatic hydrocarbon solvent may be a $C_{10}$ linear, cyclic, or branched alkane, such as n-decane, a branched decane, or a combination thereof.

In some processes, the $C_9$-$C_{11}$ non-aromatic hydrocarbon solvent is a $C_{10}$ linear, cyclic, or branched alkene.

In some processes, the $C_9$-$C_{11}$ non-aromatic hydrocarbon solvent is a $C_{10}$ linear, cyclic, or branched alkyne.

In some processes, the $C_9$-$C_{11}$ non-aromatic hydrocarbon solvent is a $C_9$ linear, cyclic, or branched alkane.

In some processes, the $C_9$-$C_{11}$ non-aromatic hydrocarbon solvent is a $C_{11}$ linear, cyclic, or branched alkane.

In some processes, the process solvent is compositionally different than the crystallization-inducing solvent. In other processes, the process solvent is compositionally similar to, or the same as, the crystallization-inducing solvent.

In some processes, the first temperature is selected from about 20° C. to about 170° C., such as from about 30° C. to about 100° C.

In some processes, the second temperature is selected from about −20° C. to about 150° C., such as from about −10° C. to about 100° C., or from about 0° C. to about 50° C.

In some processes, the temperature difference between the first temperature and the second temperature is from about 10° C. to about 200° C., such as from about 20° C. to about 100° C.

Isolating in process step (e) may utilize filtration, centrifugation, evaporation, distillation, chromatography, or a combination thereof.

In some processes, the botanical extract yield is at least 75%, calculated as mass of the precipitated botanical extract, as a percentage of total mass of the botanical extract in the solution. In various processes, the botanical extract yield is at least 80%, at least 85%, at least 90%, or at least 95%.

In some processes, the overall process botanical extract yield is at least 10%, calculated as mass of the botanical extract, as a percentage of total mass of the botanical extract contained in the starting plant material. In various processes, the overall process botanical extract yield is at least 15%, at least 20%, at least 25%, at least 30%, at least 35%, at least 40%, at least 45%, or at least 50%.

The process of isolating and recovering a botanical extract is preferably continuous or semi-continuous. In other embodiments, the process of isolating and recovering a precipitated botanical extract is a batch or semi-batch process.

In some processes of isolating and recovering a botanical extract, all steps may be conducted at a single site. In other embodiments, different process steps are conducted at different site locations.

BRIEF DESCRIPTION OF THE FIGURES

FIG. 9 is an analysis of the mother liquor containing CBD after crystallization and filtering, using high-performance liquid chromatography with diode-array detection, according to Example 1.

DETAILED DESCRIPTION OF EMBODIMENTS OF THE INVENTION

Figure 1:
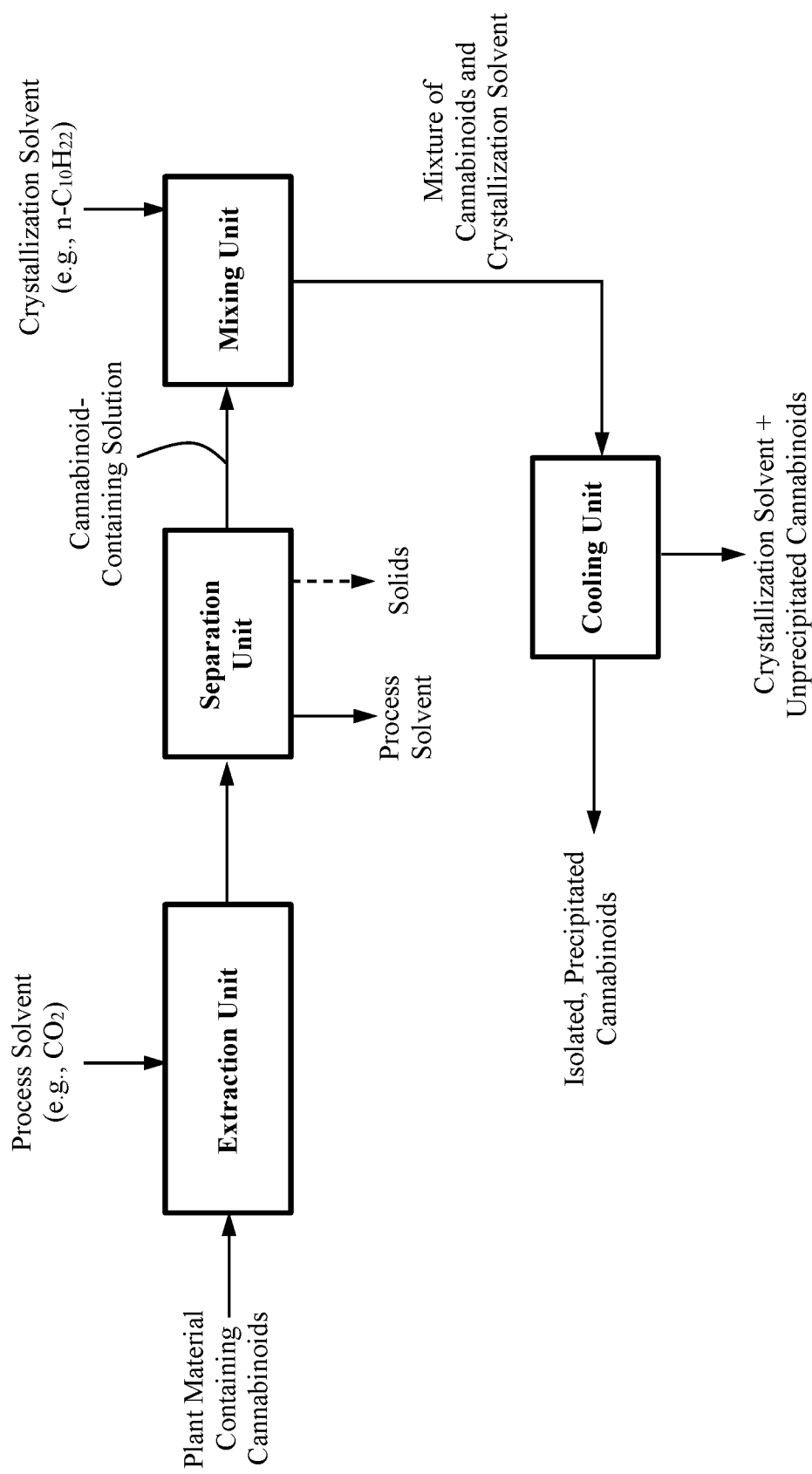
FIG. 1 is an exemplary block-flow diagram depicting a process and system for converting a plant material containing cannabinoids into isolated, precipitated cannabinoids (e.g., cannabidiol, CBD), in some embodiments employing cooling crystallization.

The solvents, methods, and systems of the present invention will be described in detail by reference to various non-limiting embodiments.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with the accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms, except when used in Markush groups. Thus in some embodiments not otherwise explicitly recited, any instance of "comprising" may be replaced by "consisting of" or, alternatively, by "consisting essentially of."

Variations of the invention are predicated on the discovery of a surprisingly effective solvent for the isolation of cannabinoids from plant extracts. The inventor has experimented with various solvents and temperatures to discover which solvents work most effectively for cannabinoid precipitation. It has been found that $C_9$ to $C_{11}$ non-aromatic hydrocarbon solvents, and especially n-decane, work very well.

Unlike lower alkanes such as pentane, n-decane does not easily combust at normal operating conditions. As the molecular size of an alkane increases, the percentage of carbon in the alkane molecules also increases. As a result, alkanes become less flammable with higher carbon number. Nonane (n-$C_9H_{20}$) is the lightest alkane to have a flash point above 25° C., and for this reason nonane is not classified as dangerously flammable whereas all alkanes $C_8$ and smaller are classified as dangerously flammable. Because of this important threshold, "higher alkanes" are often defined as alkanes having nine or more carbon atoms.

It has also been found experimentally that unlike pentane and n-heptane, n-decane is capable of causing cannabinoid precipitation at room temperature (about 25° C.) with ease and high efficiency. Precipitation at relatively high temperatures, rather than very low temperatures (e.g., −50° C.), has a positive impact on the economics. See the Example later in this specification, showing an efficiency of 90% using n-decane as the solvent for precipitation. Comparatively, pentane and n-heptane only reach a maximum efficiency of 70%, but to do so the mixture must be brought down to −50° C., which is uneconomical. Decane leads to more efficient results at a much higher temperature (up to room temperature or even higher) which is a significant economic advantage for a process of isolating cannabinoids from *Cannabis* extracts.

Not only does n-decane enable higher temperatures (reducing cooling costs) and precipitate more cannabinoids, but n-decane can also precipitate cannabinoids from a more dilute, crude feedstock. By contrast, pentane and n-heptane have been unsuccessful at isolating crystalline cannabinoids at an efficiency that is economically viable from dilute, crude feedstock.

Further experimentation has shown that there is an optimum of 9 to 11 carbon atoms in the solvent molecule. For example, the linear alkane containing 12 carbons, n-dodecane (n-$C_{12}H_{26}$), resulted in poor ability to precipitate cannabinoids. Therefore, there is an unexpected sweet spot of $C_9$ to $C_{11}$ non-aromatic hydrocarbon solvents that are superior to both $C_{8-}$ hydrocarbons as well as $C_{12+}$ hydrocarbons. Without being limited by speculation, it is believed that there is an interplay of variations in electron density of the solvent molecule, causing relatively high dipole moments across the molecule, with other intrinsic properties of hydrocarbons. For example, the boiling points of alkanes increase with increasing number of carbons. This is because the intermolecular attractive forces, although individually weak, become cumulatively more significant as the number of atoms and electrons in the molecule increases. In addition to polarity and intermolecular forces, there are differences in chemical properties including viscosity with varying numbers of carbon atoms. As the number of carbons increases, the viscosity increases, which theoretically will reduce solute mass-transfer rates in the solvent (lower Reynolds number) which in turn may reduce crystallization kinetics, potentially explaining why n-dodecane does not work as well. For small numbers of carbon atoms (e.g., 5 in pentane), while viscosity may be acceptable, the solute solubility is too high and precipitation is inefficient unless the temperature is very low. It is apparent that there are competing effects, resulting in $C_9$-$C_{11}$ being the optimum. The present invention is not, however, limited to theories or reasons why $C_9$ to $C_{11}$ non-aromatic hydrocarbon solvents are particularly effective.

Some variations of the invention provide a method of isolating one or more cannabinoids from a cannabinoid-containing solution, the method comprising contacting the cannabinoid-containing solution with a solvent comprising decane at a first temperature, to generate a mixture; cooling the mixture to reach a second temperature that is lower than the first temperature, to precipitate at least some of the cannabinoids as precipitated cannabinoids; and isolating the precipitated cannabinoids from the mixture.

In some embodiments, the cannabinoid-containing solution is obtained from a process of extracting cannabinoids from a plant material. That process may be co-located with a site at which the method is conducted, or it may be located at a distinct site. In some embodiments, the cannabinoid-containing solution is obtained from an external source. In certain embodiments, the cannabinoid-containing solution is obtained from multiple sources, such as a combination of a co-located process and an external source.

In some embodiments of the invention, the cannabinoid-containing solution contains cannabinoids from a synthetic pathway. A "synthetic pathway" means that the cannabinoid is not formed within a naturally occurring plant (e.g., *Cannabis*) but rather is formed via chemical synthesis starting with one or more precursors, in a laboratory or an industrial plant, for example. The precursors themselves may be naturally occurring or may be derived from other starting components. One example is the chemical precursor olivetol (5-pentyl-1,3-benzenediol) or its carboxylated form olivetolic acid (2,4-dihydroxy-6-pentylbenzoic acid). Olivetol may be chemically converted into tetrahydrocannabinol, for example, through a condensation reaction with $\Delta^2$-carene oxide or pulegone.

In some embodiments, the cannabinoid-containing solution is an extract or synthetic solution that contains multiple cannabinoids. In certain embodiments, the cannabinoid-containing solution is a distillate that is a type of extract in which there is only one specific type of cannabinoid. In other embodiments, the cannabinoid-containing solution is a dilute, crude feedstock containing one or more cannabinoids.

The precipitated cannabinoids may be selected from the group consisting of cannabidiol, cannabidiolic acid, cannabinol, cannabigerol, cannabichromene, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof. In certain embodiments, the precipitated cannabinoids are hydrogenated variants of any of the foregoing, acetylated variants of any of the foregoing, or a combination thereof.

In certain embodiments, the precipitated cannabinoids include cannabidiol. The cannabidiol may be at least 50 wt % or at least 90 wt %, for example, of total cannabinoid compounds contain in the precipitated cannabinoids. In various embodiments, cannabidiol (CBD) is about, or at least about, 50, 55, 60, 65, 70, 75, 80, 85, 90, 95, or 99 wt % of total cannabinoid compounds contain in the precipitated cannabinoids, including all intervening ranges.

In some methods, the first temperature is selected from about 20° C. to about 170° C., such as from about 30° C. to about 100° C. In this specification, ° C. is degrees Celsius, i.e. temperature or temperature difference on the Celsius scale. In various embodiments, the first temperature is about, at least about, or at most about 20° C., 25° C., 30° C., 35° C., 40° C., 45° C., 50° C., 60° C., 70° C., 80° C., 90° C., 100° C., 110° C., 120° C., 130° C., 140° C., 150° C., 160° C., or 170° C., including all intervening ranges. In this specification, reference to "intervening ranges" is in reference to embodiments in which there is a sub-selection of conditions within a larger range of conditions. For instance, the first temperature may specifically be sub-selected within a range of 25° C. to 90° C., 30° C. to 150° C., or any other range that starts and ends with two of the recited temperatures.

In some methods, the second temperature is selected from about −20° C. to about 150° C., such as from about −10° C. to about 100° C., or from about 0° C. to about 50° C. In various embodiments of the technology, the second temperature is about, at least about, or at most about −20° C., −15° C., −10° C., −5° C., 0° C., 5° C., 10° C., 15° C., 20° C., 25° C., 30° C., 35° C., 40° C., 45° C., 50° C., 60° C., 70° C., 80° C., 90° C., 100° C., 110° C., 120° C., 130° C., 140° C., or 150° C., including all intervening ranges.

The temperature difference between the first temperature and the second temperature is in indication of the degree of cooling that is employed in order to cause cannabinoid precipitation. In some embodiments, the temperature difference between the first temperature and the second temperature is from about 10° C. to about 200° C., such as from about 20° C. to about 100° C. In various embodiments, the temperature difference between the first temperature and the second temperature is about, at least about, or at most about 1° C., 5° C., 10° C., 15° C., 20° C., 25° C., 30° C., 35° C., 40° C., 45° C., 50° C., 60° C., 70° C., 80° C., 90° C., 100° C., 110° C., 120° C., 130° C., 140° C., 150° C., 160° C., 170° C., 180° C., 190° C., or 200° C., including all intervening ranges.

In this disclosure, unless otherwise stated, "decane" ($C_{10}H_{22}$) includes not only n-decane but also any one or more of its 74 isomers. In some embodiments, the decane is linear normal-decane ("n-decane"). In some embodiments, the decane is a branched decane. A combination of multiple decane isomers may be utilized in some embodiments. As will be described in detail, other $C_9$-$C_{11}$ hydrocarbon solvents may be employed, rather than decane or in addition to decane.

The ratio of solvent to cannabinoid-containing solution is typically selected based on the mass of desired cannabinoids (e.g., cannabidiol) within the cannabinoid-containing solution. The mass ratio of solvent to cannabinoids may vary widely, such as from about 0.1 to about 10. In various embodiments, the mass ratio of solvent to cannabinoids is about, at least about, or at most about 0.1, 0.2, 0.3, 0.4, 0.5, 0.6, 0.7, 0.75, 0.8, 0.9, 1, 1.1, 1.2, 1.3, 1.4, 1.5, 1.6, 1.7, 1.8, 1.9, 2, 2.5, 3, 3.5, 4, 5, 6, 7, 8, 9, or 10, including all intervening ranges. Generally speaking, the lowest effective ratio of solvent to cannabinoids should be employed to minimize heating, cooling, and recovery costs. The lowest effective ratio will depend on the crystallization conditions (e.g., temperature, pressure, and time). A person skilled in the chemical arts may conduct experiments to determine the optimal concentrations of solvent and cannabinoid. Design of experiments, using statistical principles, may be employed to investigate the influence of changing concentrations as well as temperature, pressure, and time, including multi-factor interactions, for example.

The step of contacting the cannabinoid-containing solution with the decane (or other $C_9$-$C_{11}$ non-aromatic hydrocarbon) solvent preferably employs some type of mixing to generate a mixture. Mixing may be accomplished using known apparatus, such as (but by no means limited to) paddle mixers, ribbon blenders, tumbling mixers, dispersers, high-shear mixers, multi-shaft mixers, planetary mixers, vertical blenders, static mixers, or homogenizers. Mixing may be continuous, semi-continuous, or in batch. Known statistical principles may be used to determine an effective mixing time in order to achieve a homogeneous mixture. In certain embodiments, mixing relies only on diffusion after contacting the cannabinoid-containing solution with the solvent in a container, without agitation, which will take longer to achieve a homogeneous solution.

In some methods, the isolating step utilizes filtration, centrifugation, evaporation, chromatography, or a combination thereof. One or more of these steps may be performed to recover the precipitated cannabinoids from the mixture, after the crystallization has occurred or potentially simultaneously with the crystallization (e.g., using apparatus for continuous crystallization and crystal removal via filters or centrifugal forces).

The cannabinoid yield may be at least 75%, calculated as mass of the precipitated cannabinoids, as a percentage of total mass of the cannabinoids in the cannabinoid-containing solution. In some embodiments, the cannabinoid yield is at least 80%, at least 85%, at least 90%, or at least 95%. In various embodiments, the cannabinoid yield is about, or at least about, 55%, 60%, 65%, 70%, 75%, 80%, 85%, 86%, 87%, 88%, 89%, 90%, 91%, 92%, 93%, 94%, 95%, 96%, 97%, 98%, or 99%, including all intervening ranges.

Other variations of the invention provide a method of isolating one or more cannabinoids from a cannabinoid-containing solution, the method comprising contacting the cannabinoid-containing solution with a $C_9$-$C_{11}$ non-aromatic hydrocarbon solvent at a first temperature, to generate a mixture; cooling the mixture to reach a second temperature that is lower than the first temperature, to precipitate at least some of the cannabinoids as precipitated cannabinoids; and isolating the precipitated cannabinoids from the mixture.

The cannabinoid-containing solution may be obtained from an external source. Alternatively, or additionally, the cannabinoid-containing solution may be obtained from a process of extracting cannabinoids from a plant material, wherein the process is optionally co-located with a site at which the crystallization method is conducted.

In some embodiments, the cannabinoid-containing solution contains cannabinoids from a synthetic pathway, wherein a cannabinoid is formed via chemical synthesis starting with one or more precursors. The precursors themselves may be naturally occurring or may be derived from other starting components. One example is the chemical precursor olivetol (5-pentyl-1,3-benzenediol) or its carboxylated form olivetolic acid (2,4-dihydroxy-6-pentylbenzoic acid). Olivetol may be chemically converted into tetrahydrocannabinol, for example, through a condensation reaction with $\Delta^2$-carene oxide or pulegone.

The precipitated cannabinoids may be selected from the group consisting of cannabidiol, cannabidiolic acid, cannabinol, cannabigerol, cannabichromene, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof.

When the precipitated cannabinoids include cannabidiol, such cannabidiol may be at least 50 wt % of total cannabinoid compounds contain in the precipitated cannabinoids. In some embodiments, the cannabidiol is at least 90 wt % of total cannabinoid compounds contain in the precipitated cannabinoids. In various embodiments, the cannabidiol is about, or at least about, 50%, 55%, 60%, 65%, 70%, 75%, 80%, 85%, 90%, 95%, or 99%, including all intervening ranges, of total cannabinoid compounds contain in the precipitated cannabinoids.

The $C_9$-$C_{11}$ non-aromatic hydrocarbon solvent is a crystallization-inducing solvent. By "crystallization-inducing" it is meant that the solvent is capable of causing precipitation of cannabinoids. Generally, $C_9$-$C_{11}$ non-aromatic hydrocarbons may be alkanes (only single C—C bonds present), alkenes (one or more C=C double bonds present), or alkynes (one or more C≡C triple bonds present) and may be linear, cyclic, or branched.

In some embodiments, the solvent is a $C_{10}$ non-aromatic hydrocarbon solvent. Especially preferred are $C_{10}$ alkanes, which are decane and any of its isomers. That is, in preferred embodiments, the solvent is selected from the group consisting of n-decane, 2-methylnonane, 3-methylnonane, 4-methylnonane, 5-methylnonane, 3-ethyloctane, 4-ethyloctane, 2,2-dimethyloctane, 2,3-dimethyloctane, 2,4-dimethyloctane, 2,5-dimethyloctane, 2,6-dimethyloctane, 2,7-dimethyloctane, 3,3-dimethyloctane, 3,4-dimethyloctane, 3,5-dimethyloctane, 3,6-dimethyloctane, 4,4-dimethyloctane, 4,5-dimethyloctane, 4-propylheptane, 4-isopropylheptane, 2-methyl-3-ethylheptane, 2-methyl-4-ethylheptane, 2-methyl-5-ethylheptane, 3-methyl-3-ethylheptane, 3-methyl-4-ethylheptane, 3-methyl-5-ethylheptane, 4-methyl-3-ethylheptane, 4-methyl-4-ethylheptane, 2,2,3-trimethylheptane, 2,2,4-trimethylheptane, 2,2,5-trimethylheptane, 2,2,6-trimethylheptane, 2,3,3-trimethylheptane, 2,3,4-trimethylheptane, 2,3,5-trimethylheptane, 2,3,6-trimethylheptane, 2,4,4-trimethylheptane, 2,4,5-trimethylheptane, 2,4,6-trimethylheptane, 2,5,5-trimethylheptane, 3,3,4-trimethylheptane, 3,3,5-trimethylheptane, 3,4,4-trimethylheptane, 3,4,5-trimethylheptane, 2-methyl-3-isopropylhexane, 3,3-diethylhexane, 3,4-diethylhexane, 2,2-dimethyl-3-ethylhexane, 2,2-dimethyl-4-ethylhexane, 2,3-dimethyl-3-ethylhexane, 2,3-dimethyl-4-ethylhexane, 2,4-dimethyl-3-ethylhexane, 2,4-dimethyl-4-ethylhexane, 2,5-dimethyl-3-ethylhexane, 3,3-dimethyl-4-ethylhexane, 3,4-dimethyl-3-ethylhexane, 2,2,3,3-tetramethylhexane, 2,2,3,4-tetramethylhexane, 2,2,3,5-tetramethylhexane, 2,2,4,4-tetramethylhexane, 2,2,4,5-tetramethylhexane, 2,2,5,5- tetramethylhexane, 2,3,3,4-tetramethylhexane, 2,3,3,5-tetramethylhexane, 2,3,4,4-tetramethylhexane, 2,3,4,5-tetramethylhexane, 3,3,4,4-tetramethylhexane, 2,4-dimethyl-3-isopropylpentane, 2-methyl-3,3-diethylpentane, 2,2,3-trimethyl-3-ethylpentane, 2,2,4-trimethyl-3-ethylpentane, 2,3,4-trimethyl-3-ethylpentane, 2,2,3,3,4-pentamethylpentane, 2,2,3,4,4-pentamethylpentane, and combinations thereof. In certain preferred embodiments, the solvent is specifically n-decane, n-$C_{10}H_{22}$, or is a solvent comprising n-decane.

In some embodiments, the $C_9$-$C_{11}$ non-aromatic hydrocarbon solvent is a $C_{10}$ linear, cyclic, or branched alkane solvent. Linear or branched $C_{10}$ alkanes generally have the formula $C_{10}H_{22}$, while cyclic $C_{10}$ alkanes have less hydrogen (e.g., cyclodecane is $C_{10}H_{20}$).

In some embodiments, the $C_9$-$C_{11}$ non-aromatic hydrocarbon solvent is a $C_{10}$ linear, cyclic, or branched alkene solvent. An alkene contains at least one carbon-carbon double bond, C=C. Exemplary $C_{10}$ alkenes are 1-decene or 4-decene, for instance. Linear or branched $C_{10}$ single alkenes generally have the formula $C_{10}H_{20}$, while cyclic $C_{10}$ alkenes have less hydrogen.

In some embodiments, the $C_9$-$C_{11}$ non-aromatic hydrocarbon solvent is a $C_{10}$ linear, cyclic, or branched alkyne solvent. An alkyne contains at least one carbon-carbon triple bond, C≡C. Exemplary $C_{10}$ alkynes are 1-decyne and 2-decyne, for instance. Linear or branched $C_{10}$ single alkynes generally have the formula $C_{10}H_{18}$, while cyclic $C_{10}$ alkynes have less hydrogen.

In some embodiments, the $C_9$-$C_{11}$ non-aromatic hydrocarbon solvent is a $C_9$ linear, cyclic, or branched alkane solvent, a $C_9$ linear, cyclic, or branched alkene solvent, a $C_9$ linear, cyclic, or branched alkyne solvent, or a combination thereof. Examples of $C_9$ solvents include n-nonane, 1-nonene, 1-nonyne, and bicyclo[3.3.1]nonane. Linear and branched $C_9$ alkanes generally have the formula $C_9H_{20}$, linear and branched $C_9$ single alkenes generally have the formula $C_9H_{18}$, and linear and branched $C_9$ single alkynes generally have the formula $C_9H_{16}$.

In some embodiments, the $C_9$-$C_{11}$ non-aromatic hydrocarbon solvent is a $C_{11}$ linear, cyclic, or branched alkane solvent, a $C_{11}$ linear, cyclic, or branched alkene solvent, a $C_{11}$ linear, cyclic, or branched alkyne solvent, or a combination thereof. Examples of $C_{11}$ solvents include n-undecane, 5-undecene, and 3-undecyne. Linear and branched $C_{11}$ alkanes generally have the formula $C_{11}H_{24}$, linear and branched $C_{11}$ single alkenes generally have the formula $C_{11}H_{22}$, and linear and branched $C_{11}$ single alkynes generally have the formula $C_{11}H_{20}$.

In this disclosure, "cyclic" also includes polycyclic structures, such as bicyclo structures. Bicyclo compounds are a class of saturated compounds consisting of two fused rings, having two or more atoms in common, and that take the name of an open-chain hydrocarbon containing the same total number of atoms. Examples include bicyclo[6.1.1]decane, $C_{10}H_{18}$ and 2-methylbicyclo[4.2.2]decane, $C_{11}H_{20}$.

$C_9$ to $C_{11}$ aromatic hydrocarbon solvents (e.g., n-butylbenzene, $C_{10}H_{14}$) are not expected to work as well as $C_9$ to $C_{11}$ non-aromatic hydrocarbon solvents, since an aromatic group requires at least 6 carbon atoms and there would be 3 to 5 carbon atoms potentially forming an alkyl side group. The aromatic nature is expected to significantly alter the chemical properties including solubility of cannabinoids. Notwithstanding that aromatics are not preferred, there may be some aromatic content included in the solvent when a mixture of different molecules is present.

The $C_9$-$C_{11}$ non-aromatic hydrocarbon solvent may be a single molecule or a mixture of two or more molecules, such as 2, 3, 4, 5, 6, 7, 8, 9, or more distinct molecules. When there are multiple molecules, they may all be $C_9$, all $C_{10}$, all $C_{11}$, a mix of $C_9$ and $C_{10}$, a mix of $C_{10}$ or $C_{11}$, or a mix of $C_9$, $C_{10}$, and $C_{11}$.

The $C_9$-$C_{11}$ non-aromatic hydrocarbon solvent preferably has a purity of at least 90 wt %, at least 95 wt %, at least 99 wt %, or at least 99.9 wt %. Impurities in the $C_9$-$C_{11}$ non-aromatic hydrocarbon solvent may include water, dirt, salts, ash, and other hydrocarbons. When other hydrocarbons are present as impurities, those other hydrocarbons may be in a different class than $C_9$-$C_{11}$ non-aromatic hydrocarbons. For example, when a cyclic alkane (e.g., n-butylcyclohexane) is used in the solvent, there may be aromatic impurities (e.g., n-butylbenzene) arising from the original process to make the saturated cyclic hydrocarbon.

In some methods employing cooling crystallization out of a $C_9$-$C_{11}$ non-aromatic hydrocarbon solvent, the first temperature is selected from about 20° C. to about 170° C., such as from about 30° C. to about 100° C. In various embodiments, the first temperature is about, at least about, or at most about 20° C., 25° C., 30° C., 35° C., 40° C., 45° C., 50° C., 60° C., 70° C., 80° C., 90° C., 100° C., 110° C., 120° C., 130° C., 140° C., 150° C., 160° C., or 170° C., including all intervening ranges.

In some methods employing cooling crystallization out of a $C_9$-$C_{11}$ non-aromatic hydrocarbon solvent, the second temperature is selected from about −20° C. to about 150° C., such as from about −10° C. to about 100° C., or from about 0° C. to about 50° C. In various embodiments of the technology, the second temperature is about, at least about, or at most about −20° C., −15° C., −10° C., −5° C., 0° C., 5° C., 10° C., 15° C., 20° C., 25° C., 30° C., 35° C., 40° C., 45° C., 50° C., 60° C., 70° C., 80° C., 90° C., 100° C., 110° C., 120° C., 130° C., 140° C., or 150° C., including all intervening ranges.

In some embodiments employing cooling crystallization out of a $C_9$-$C_{11}$ non-aromatic hydrocarbon solvent, the temperature difference between the first temperature and the second temperature is from about 10° C. to about 200° C., such as from about 20° C. to about 100° C. In various embodiments, the temperature difference between the first temperature and the second temperature is about, at least about, or at most about 1° C., 5° C., 10° C., 15° C., 20° C., 25° C., 30° C., 35° C., 40° C., 45° C., 50° C., 60° C., 70° C., 80° C., 90° C., 100° C., 110° C., 120° C., 130° C., 140° C., 150° C., 160° C., 170° C., 180° C., 190° C., or 200° C., including all intervening ranges.

The ratio of $C_9$-$C_{11}$ non-aromatic hydrocarbon solvent to cannabinoid-containing solution is typically selected based on the mass of desired cannabinoids (e.g., CBD) within the cannabinoid-containing solution. The mass ratio of solvent to cannabinoids may vary widely, such as from about 0.1 to about 10. In various embodiments, the mass ratio of solvent to cannabinoids is about, at least about, or at most about 0.1, 0.2, 0.3, 0.4, 0.5, 0.6, 0.7, 0.75, 0.8, 0.9, 1, 1.1, 1.2, 1.3, 1.4, 1.5, 1.6, 1.7, 1.8, 1.9, 2, 2.5, 3, 3.5, 4, 5, 6, 7, 8, 9, or 10. Generally speaking, the lowest effective ratio of $C_9$-$C_{11}$ non-aromatic hydrocarbon solvent to cannabinoids should be employed to minimize heating, cooling, and recovery costs. The lowest effective ratio will depend on the crystallization conditions (e.g., temperature, pressure, and time). A person skilled in the chemical arts may conduct experiments to determine the optimal concentrations of solvent and cannabinoid. Design of experiments, using statistical principles, may be employed to investigate the influence of changing concentrations as well as temperature, pressure, and time, including multi-factor interactions, for example.

In various methods, the isolating step utilizes filtration, centrifugation, evaporation, chromatography, or a combination thereof. One or more of these steps may be performed to recover the precipitated cannabinoids from the mixture, after the crystallization has occurred or potentially simultaneously with the crystallization (e.g., using apparatus for continuous crystallization and crystal removal via filters or centrifugal forces).

The cannabinoid yield may be at least 75%, calculated as mass of the precipitated cannabinoids, as a percentage of total mass of the cannabinoids in the cannabinoid-containing solution. In some embodiments, the cannabinoid yield is at least 80%, is at least 85%, at least 90%, or at least 95%. In various embodiments employing cooling crystallization out of a $C_9$-$C_{11}$ non-aromatic hydrocarbon solvent, the cannabinoid yield is about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, including all intervening ranges.

Some variations are premised on evaporative crystallization, rather than cooling crystallization, of cannabinoids in order to induce precipitation. In some variations, the invention provides a method of isolating one or more cannabinoids from a cannabinoid-containing solution, the method comprising contacting the cannabinoid-containing solution with a solvent comprising decane at a first temperature below the decane boiling point, to generate a mixture; subjecting the mixture to a second temperature that causes vaporization of the solvent, to precipitate at least some of the cannabinoids as precipitated cannabinoids; and isolating the precipitated cannabinoids from the mixture.

The cannabinoid-containing solution may be obtained from an external source. Alternatively, or additionally, the cannabinoid-containing solution may be obtained from a process of extracting cannabinoids from a plant material, wherein the process is optionally co-located with a site at which the evaporative-crystallization method is conducted.

In some embodiments, the cannabinoid-containing solution contains cannabinoids from a synthetic pathway, wherein a cannabinoid is formed via chemical synthesis starting with one or more precursors. The precursors themselves may be naturally occurring or may be derived from other starting components.

When using evaporative crystallization, the step of contacting the cannabinoid-containing solution with the decane (or other $C_9$-$C_{11}$ non-aromatic hydrocarbon) solvent may employ some type of mixing to generate a mixture, or may rely on simple diffusion. Mixing may be accomplished using known apparatus, such as (but by no means limited to) paddle mixers, ribbon blenders, tumbling mixers, dispersers, high-shear mixers, multi-shaft mixers, planetary mixers, vertical blenders, static mixers, or homogenizers. Mixing may be continuous, semi-continuous, or in batch. Known statistical principles may be used to determine an effective mixing time in order to achieve a homogeneous mixture.

The precipitated cannabinoids may be selected from the group consisting of cannabidiol, cannabidiolic acid, cannabinol, cannabigerol, cannabichromene, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof.

When the precipitated cannabinoids include cannabidiol, such cannabidiol may be at least 50 wt % of total cannabinoid compounds contain in the precipitated cannabinoids. In some embodiments, the cannabidiol is at least 90 wt % of total cannabinoid compounds contain in the precipitated cannabinoids.

In some embodiments employing evaporative crystallization, the decane is n-decane. In some embodiments, the decane is a branched decane. A combination of multiple decane isomers may be utilized.

In some methods employing evaporative crystallization, the first temperature is selected from about 20° C. to about 170° C., such as from about 30° C. to about 100° C. In various embodiments, the first temperature is about, at least about, or at most about 20° C., 25° C., 30° C., 35° C., 40° C., 45° C., 50° C., 60° C., 70° C., 80° C., 90° C., 100° C., 110° C., 120° C., 130° C., 140° C., 150° C., 160° C., or 170° C., including all intervening ranges.

In some methods employing evaporative crystallization, the second temperature is selected from about 25° C. to about 250° C., such as from about 100° C. to about 200° C. In various embodiments, the second temperature is about, at least about, or at most about 25° C., 30° C., 40° C., 50° C., 60° C., 70° C., 80° C., 90° C., 100° C., 110° C., 120° C., 130° C., 140° C., 150° C., 160° C., 170° C., 175° C., 180° C., 190° C., or 200° C., including all intervening ranges.

The pressure of evaporative crystallization is preferably selected as a function of the specific decane isomer being used (in embodiments employing decane as the solvent). In various embodiments, the pressure for evaporative crystallization is about, at least about, or at most about 0.01 atm, 0.05 atm, 0.1 atm, 0.5 atm, 1 atm, 1.5 atm, 2 atm, 3 atm, 4 atm, or 5 atm, including all intervening ranges.

In some embodiments relating to evaporative crystallization, the second temperature is increased and/or the pressure is decreased over time. For example, the pressure may be gradually decreased to higher levels of vacuum, causing increasing extents of evaporative crystallization over time.

The ratio of decane (or other $C_9$-$C_{11}$ non-aromatic hydrocarbon) solvent to cannabinoid-containing solution is typically selected based on the mass of desired cannabinoids (e.g., CBD) within the cannabinoid-containing solution. The mass ratio of solvent to cannabinoids may vary widely, such as from about 0.1 to about 10. In various embodiments, the mass ratio of solvent to cannabinoids is about, at least about, or at most about 0.1, 0.2, 0.3, 0.4, 0.5, 0.6, 0.7, 0.75, 0.8, 0.9, 1, 1.1, 1.2, 1.3, 1.4, 1.5, 1.6, 1.7, 1.8, 1.9, 2, 2.5, 3, 3.5, 4, 5, 6, 7, 8, 9, or 10, including all intervening ranges. Generally speaking, the lowest effective ratio of solvent to cannabinoids should be employed to minimize heating, cooling, and recovery costs. The lowest effective ratio will depend on the evaporative crystallization conditions (e.g., temperature, pressure, and time).

In some methods utilizing evaporative crystallization, the isolating step utilizes filtration, centrifugation, evaporation, chromatography, or a combination thereof. One or more of these steps may be performed to recover the precipitated cannabinoids from the mixture, after the crystallization has occurred or potentially simultaneously with the crystallization (e.g., using apparatus for continuous evaporation, crystallization, and crystal removal via filters or centrifugal forces).

The cannabinoid yield when employing evaporative crystallization may be at least 60%, calculated as mass of the precipitated cannabinoids, as a percentage of total mass of the cannabinoids in the cannabinoid-containing solution. In some embodiments, the cannabinoid yield is at least 65%, at least 70%, at least 75%, at least 80%, at least 85%, or at least 90%.

Other variations of the invention provide a method of isolating one or more cannabinoids from a cannabinoid-containing solution, the method comprising contacting the cannabinoid-containing solution with a $C_9$-$C_{11}$ non-aromatic hydrocarbon solvent at a first temperature below the solvent boiling point, to generate a mixture; subjecting the mixture to a second temperature that causes vaporization of the solvent, to precipitate at least some of the cannabinoids as precipitated cannabinoids; and isolating the precipitated cannabinoids from the mixture.

The cannabinoid-containing solution may be obtained from an external source. Alternatively, or additionally, the cannabinoid-containing solution may be obtained from a process of extracting cannabinoids from a plant material, wherein the process may be co-located with a site at which the crystallization method is conducted.

In some embodiments, the cannabinoid-containing solution contains cannabinoids from a synthetic pathway, wherein a cannabinoid is formed via chemical synthesis starting with one or more precursors. The precursors themselves may be naturally occurring or may be derived from other starting components.

The precipitated cannabinoids may be selected from the group consisting of cannabidiol, cannabidiolic acid, cannabinol, cannabigerol, cannabichromene, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof.

When the precipitated cannabinoids include cannabidiol, such cannabidiol may be at least 50 wt % of total cannabinoid compounds contain in the precipitated cannabinoids. In some embodiments, the cannabidiol is at least 90 wt % of total cannabinoid compounds contain in the precipitated cannabinoids.

The $C_9$-$C_{11}$ non-aromatic hydrocarbon solvent may be selected from the group consisting of a $C_{10}$ linear, cyclic, or branched alkane solvent; a $C_{10}$ linear, cyclic, or branched alkene solvent; a $C_{10}$ linear, cyclic, or branched alkyne solvent; a $C_9$ linear, cyclic, or branched alkane solvent; a $C_9$ linear, cyclic, or branched alkene solvent; a $C_9$ linear, cyclic, or branched alkyne solvent; a $C_{11}$ linear, cyclic, or branched alkane solvent; a $C_{11}$ linear, cyclic, or branched alkene solvent; a $C_{11}$ linear, cyclic, or branched alkyne solvent; and combinations thereof.

In some embodiments employing evaporative crystallization, the solvent is selected from the group consisting of n-decane, 2-methylnonane, 3-methylnonane, 4-methylnonane, 5-methylnonane, 3-ethyloctane, 4-ethyloctane, 2,2-dimethyloctane, 2,3-dimethyloctane, 2,4-dimethyloctane, 2,5-dimethyloctane, 2,6-dimethyloctane, 2,7-dimethyloctane, 3,3-dimethyloctane, 3,4-dimethyloctane, 3,5-dimethyloctane, 3,6-dimethyloctane, 4,4-dimethyloctane, 4,5-dimethyloctane, 4-propylheptane, 4-isopropylheptane, 2-methyl-3-ethylheptane, 2-methyl-4-ethylheptane, 2-methyl-5-ethylheptane, 3-methyl-3-ethylheptane, 3-methyl-4-ethylheptane, 3-methyl-5-ethylheptane, 4-methyl-3-ethylheptane, 4-methyl-4-ethylheptane, 2,2,3-trimethylheptane, 2,2,4-trimethylheptane, 2,2,5-trimethylheptane, 2,2,6-trimethylheptane, 2,3,3-trimethylheptane, 2,3,4-trimethylheptane, 2,3,5-trimethylheptane, 2,3,6-trimethylheptane, 2,4,4-trimethylheptane, 2,4,5-trimethylheptane, 2,4,6-trimethylheptane, 2,5,5-trimethylheptane, 3,3,4-trimethylheptane, 3,3,5-trimethylheptane, 3,4,4-trimethylheptane, 3,4,5-trimethylheptane, 2-methyl-3-isopropylhexane, 3,3-diethylhexane, 3,4-diethylhexane, 2,2-dimethyl-3-ethylhexane, 2,2-dimethyl-4-ethylhexane, 2,3-dimethyl-3-ethylhexane, 2,3-dimethyl ethylhexane, 2,4-dimethyl-3-ethylhexane, 2,4-dimethyl-4-ethylhexane, 2,5-dimethyl ethylhexane, 3,3-dimethyl-4-ethylhexane, 3,4-dimethyl-3-ethylhexane, 2,2,3,3-tetramethylhexane, 2,2,3,4-tetramethylhexane, 2,2,3,5-tetramethylhexane, 2,2,4,4-tetramethylhexane, 2,2,4,5-tetramethylhexane, 2,2,5,5-tetramethylhexane, 2,3,3,4-tetramethylhexane, 2,3,3,5-tetramethylhexane, 2,3,4,4-tetramethylhexane, 2,3,4,5-tetramethylhexane, 3,3,4,4-tetramethylhexane, 2,4-dimethyl-3-isopropylpentane, 2-methyl-3,3-diethylpentane, 2,2,3-trimethyl-3-ethylpentane, 2,2,4-trimethyl-3-ethylpentane, 2,3,4-trimethyl-3-ethylpentane, 2,2,3,3,4-pentamethylpentane, 2,2,3,4,4-pentamethylpentane, and combinations thereof. In certain preferred embodiments, the solvent is specifically n-decane, or is a solvent comprising n-decane.

In some methods employing evaporative crystallization from a $C_9$-$C_{11}$ non-aromatic hydrocarbon solvent, the first temperature is selected from about 20° C. to about 170° C., such as from about 30° C. to about 100° C. In various embodiments, the first temperature is about, at least about, or at most about 20° C., 25° C., 30° C., 35° C., 40° C., 45° C., 50° C., 60° C., 70° C., 80° C., 90° C., 100° C., 110° C., 120° C., 130° C., 140° C., 150° C., 160° C., or 170° C., including all intervening ranges.

In some methods employing evaporative crystallization from a $C_9$-$C_{11}$ non-aromatic hydrocarbon solvent, the second temperature is selected from about 25° C. to about 250° C., such as from about 100° C. to about 200° C. In various embodiments, the second temperature is about, at least about, or at most about 25° C., 30° C., 40° C., 50° C., 60° C., 70° C., 80° C., 90° C., 100° C., 110° C., 120° C., 130° C., 140° C., 150° C., 160° C., 170° C., 175° C., 180° C., 190° C., or 200° C., including all intervening ranges.

The pressure of evaporative crystallization from a $C_9$-$C_{11}$ non-aromatic hydrocarbon solvent is preferably selected as a function of the specific solvent being used. As is well-known, at a fixed pressure, higher temperatures cause vaporization of a liquid solvent. As the pressure increases, the temperature required to vaporize the solvent also increases, at vapor-liquid equilibrium. The normal boiling point for a solvent is the vaporization temperature at atmospheric pressure (1 bar). At lower pressures, under vacuum, the vaporization temperature is lower than the normal boiling point, while at elevated pressures (>1 bar), the vaporization temperature is higher than the normal boiling point. One skilled in the art can select the second temperature for a given solvent and then determine what pressure allows reasonable vaporization to occur (in order to cause precipitation). Alternatively, one skilled in the art can select a desired pressure, such as atmospheric pressure, and then determine what temperature will cause vaporization of the solvent (in to cause precipitation). In various embodiments, the pressure for evaporative crystallization is about, at least about, or at most about 0.01 bar, 0.05 bar, 0.1 bar, 0.5 bar, 1 bar, 1.5 bar, 2 bar, 3 bar, 4 bar, or 5 bar, for example.

The isolating step may utilize one or more of filtration, centrifugation, evaporation, or chromatography. One or more of these steps may be performed to recover the precipitated cannabinoids from the mixture, after the crystallization has occurred or potentially simultaneously with the crystallization (e.g., using apparatus for continuous crystallization and crystal removal with filters or centrifugal forces).

The cannabinoid yield may be at least 75%, calculated as mass of the precipitated cannabinoids, as a percentage of total mass of the cannabinoids in the cannabinoid-containing solution. In some embodiments, the cannabinoid yield is at least 80%, at least 85%, at least 90%, or at least 95%.

Certain embodiments utilize a hybrid approach with both cooling-induced crystallization as well as evaporative crystallization. In such embodiments, in order to both cool the solvent as well as evaporate the solvent at the same time, the pressure must be reduced. Therefore, these hybrid embodiments typically employ vacuum evaporation of solvent. In principle, a pressure higher than 1 atm could be used when a high first temperature is employed and the second temperature is selected such that there is both cooling crystallization as well as evaporative crystallization. Evaporation itself can cause cooling since evaporation consumes heat.

It will also be recognized that cooling-induced crystallization and evaporative crystallization may be conducted in sequence, in certain embodiments. For example, cooling crystallization may be performed first, followed by evaporative crystallization. Evaporative crystallization followed by cooling crystallization would only work if less than all the solvent evaporates initially (so that there is still solvent to be cooled in the second step), or if additional solvent is added after the first step. In these sequential approaches, there may or may not be intermediate recovery of precipitated cannabinoids between cooling crystallization and evaporative crystallization (in either order). The final, precipitated cannabinoids are isolated and recovered.

Variations of the invention provide a process for producing cannabinoids from a cannabinoid-containing plant material, the process comprising:

(a) providing a starting cannabinoid-containing plant material;

(b) exposing the starting cannabinoid-containing plant material to a process solvent, thereby forming a cannabinoid-containing solution containing cannabinoids dissolved and/or suspended in the process solvent;

(c) contacting the cannabinoid-containing solution with a crystallization-inducing solvent comprising decane, or another $C_9$-$C_{11}$ non-aromatic hydrocarbon, at a first temperature, to generate a mixture;

(d) cooling the mixture to reach a second temperature that is lower than the first temperature, to precipitate at least some of the cannabinoids as precipitated cannabinoids; and (e) isolating and recovering the precipitated cannabinoids from the mixture.

FIG. 1 is an exemplary block-flow diagram depicting a process and system for converting a plant material containing cannabinoids into isolated, precipitated cannabinoids (e.g., CBD), in some embodiments employing cooling crystallization. In all drawings herein, dotted lines denote optional streams and units.

The cannabinoid-containing plant material may be selected from *Cannabis sativa*, *Cannabis indica*, *Cannabis ruderalis*, *Echinacea purpurea*, *Echinacea angustifolia*, *Acmella oleracea*, *Helichrysum umbraculigerum*, or *Radula marginata*. In typical embodiments, the cannabinoid-containing plant material is selected from the *Cannabis* genus, including the specific species *Cannabis sativa*, *Cannabis indica*, and *Cannabis ruderalis*.

Phytocannabinoids are known to occur in several plant species besides those in the *Cannabis* genus. These non-*Cannabis* species include *Echinacea purpurea*, *Echinacea angustifolia*, *Acmella oleracea*, *Helichrysum umbraculigerum*, and *Radula marginata*. Well-known cannabinoids that are not derived from *Cannabis* are lipophilic alkylamides from *Echinacea* species—most notably dodeca-2E,4E, 8Z,10E/Z-tetraenoic acid isobutylamide.

The precipitated cannabinoids may be selected from the group consisting of cannabidiol, cannabidiolic acid, cannabinol, cannabigerol, cannabichromene, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof.

In some embodiments, the precipitated cannabinoids include cannabidiol. The cannabidiol may at least 50 wt %, or at least 90 wt %, of total cannabinoid compounds contain in the precipitated cannabinoids, for example.

The process solvent may be supercritical carbon dioxide. The process solvent may be a non-polar solvent. The process solvent may be a hydrocarbon, such as a $C_2$-$C_8$ alkane. The process solvent may be a $C_1$-$C_{12}$ alcohol, such as ethanol. In some embodiments, the process solvent is not a $C_9$-$C_{11}$ non-aromatic hydrocarbon. In certain embodiments, the process solvent is not a $C_{10}$ alkane. In certain embodiments, the process solvent is not n-decane. In typical embodiments, the process solvent is different than the crystallization-inducing solvent. In certain embodiments, the process solvent is the same compound as the crystallization-inducing solvent, but the process solvent may or may not still be present when the crystallization-inducing solvent is added in step (c). The process solvent may be removed, at least in part, prior to step (c). In some embodiments, the crystallization-inducing solvent is or includes n-decane. In some embodiments, the crystallization-inducing solvent is or includes branched decane(s).

In some process embodiments, the process solvent is a hydrocarbon solvent selected from the group consisting of propane, isobutane, n-hexane, cyclohexane, cyclohexene, toluene, xylenes, vegetable oils, and combinations thereof, for example. Dilution gases may be included with the process solvent. For example, inert gases such as Ar or $N_2$ may be present. A pump, such as a centrifugal pump, a positive-displacement pump, an axial-flow pump, etc., may be used to introduce the process solvent in step (b). The process solvent may be removed, at least in part, prior to step (c).

Selection of extraction conditions in step (b) will generally depend on the desired product(s) and choice of process solvent. In some embodiments, the extraction pressure in step (b) is selected from about 1 atm to about 500 atm. In various embodiments, the extraction pressure is about, at least about, or at most about 1, 2, 3, 4, 5, 10, 15, 20, 25, 30, 40, 50, 60, 70, 80, 90, 100, 150, 200, 250, 300, 350, 400, 450, or 500 atm, for example. The extraction time in step (b) may be from about 0.1 minute to about 1 hour, for example. In various embodiments, the extraction time is about, at least about, or at most about 0.1, 0.2, 0.3, 0.4, 0.5, 1, 2, 3, 4, 5, 10, 15, 20, 25, 30, 40, 50, or 60 minutes, for example. The extraction time refers to the amount of time needed for the extraction to take place, once the extraction pressure and temperature are reached. Step (b) may be carried out at an extraction temperature from about 25° C. to about 100° C., for example. In various embodiments, the extraction temperature is about, at least about, or at most about 25° C., 30° C., 40° C., 50° C., 55° C., 60° C., 65° C., 70° C., 80° C., 90° C., or 95° C.

In step (b), there may also be generation of residual solids from which the cannabinoids had been extracted. The residual solids generated during the process may be collected from the extraction vessel (step (b)) and may be combusted to generate energy, composted as a soil amendment, utilized as animal feed, or used for other purposes.

The first temperature in step (c) may be selected from about 20° C. to about 170° C., such as from about 30° C. to about 100° C. The second temperature in step (d) may be selected from about −20° C. to about 150° C., such as from about −10° C. to about 100° C., or from about 0° C. to about 50° C. The temperature difference between the first temperature and the second temperature may be from about 10° C. to about 200° C., such as from about 20° C. to about 100° C.

Isolating in step (e) may utilize one or more of filtration, centrifugation, evaporation, or chromatography. One or more of these steps may be performed to recover the precipitated cannabinoids from the mixture, after the crystallization has occurred. Alternatively, or additionally, one or more of these steps may be performed to recover the precipitated cannabinoids simultaneously with the crystallization. In one such example, step (e) employs an apparatus for continuous crystallization and crystal removal with a filter, centrifugal forces, or both of a filter (or multiple filters) plus centrifugal forces. An example of such an apparatus is a Nutsche unit.

In various processes, the cannabinoid yield is at least 75%, calculated as mass of the precipitated cannabinoids, as a percentage of total mass of the cannabinoids in the cannabinoid-containing solution formed in step (b). In some processes, the cannabinoid yield is at least 80%, at least 85%, at least 90%, or at least 95%.

An overall process cannabinoid yield can also be calculated as mass of the precipitated cannabinoids, as a percentage of total mass of the cannabinoids contained in the starting cannabinoid-containing plant material provided in step (a). The overall process cannabinoid yield may be at least 50%, at least 60%, at least 70%, at least 80%, or at least 90%, for example.

The process is preferably continuous or semi-continuous. It is also possible to conduct the process batchwise, or a combination of batch and continuous steps. In some embodiments, all process steps are conducted at a single site. In other embodiments, there are at least two different sites across which a process is carried out.

Some variations provide a process for producing cannabinoids from cannabinoid precursors, the process comprising:

(a) providing one or more cannabinoid precursors;

(b) chemically converting the cannabinoid precursors into cannabinoids, thereby forming a cannabinoid-containing solution;

(c) contacting the cannabinoid-containing solution with a crystallization-inducing solvent comprising decane, or another $C_9$-$C_{11}$ non-aromatic hydrocarbon, at a first temperature, to generate a mixture;

(d) cooling the mixture to reach a second temperature that is lower than the first temperature, to precipitate at least some of the cannabinoids as precipitated cannabinoids; and (e) isolating and recovering the precipitated cannabinoids from the mixture.

Other variations provide a process employing evaporative crystallization for producing cannabinoids from a cannabinoid-containing plant material, the process comprising:

(a) providing a starting cannabinoid-containing plant material;

(b) exposing the starting cannabinoid-containing plant material to a process solvent, thereby forming a cannabinoid-containing solution containing cannabinoids dissolved and/or suspended in the process solvent;

(c) contacting the cannabinoid-containing solution with a crystallization-inducing solvent comprising decane, or another $C_9$-$C_{11}$ non-aromatic hydrocarbon, at a first temperature below the solvent boiling point, to generate a mixture;

(d) vaporizing the crystallization-inducing solvent at a second temperature that is higher than the solvent boiling point at the pressure during this step, to precipitate at least some of the cannabinoids as precipitated cannabinoids; and (e) isolating and recovering the precipitated cannabinoids from the mixture.

Figure 2:
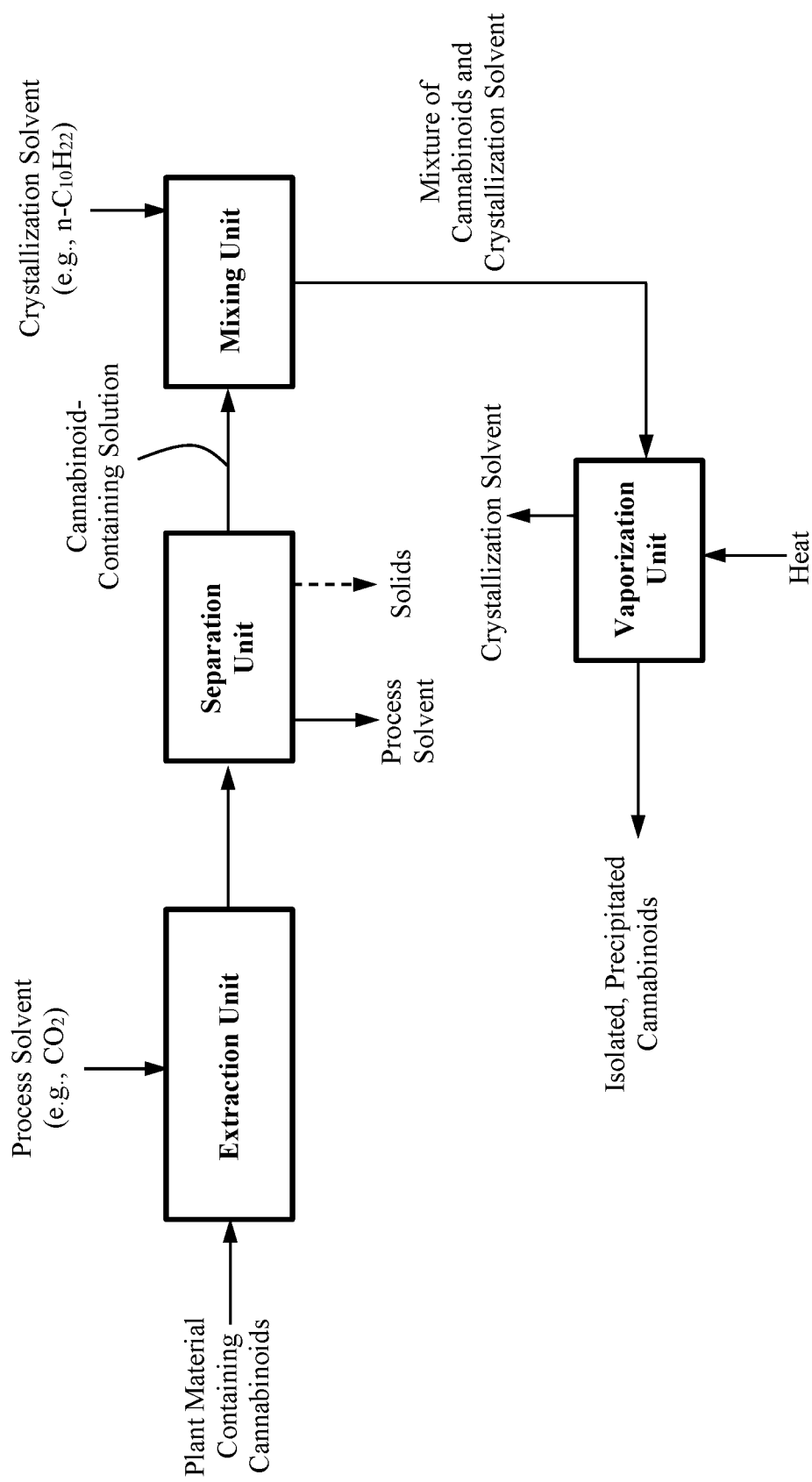
FIG. 2 is an exemplary block-flow diagram depicting a process and system for converting a plant material containing cannabinoids into isolated, precipitated cannabinoids (e.g., CBD), in some embodiments employing evaporative crystallization.

FIG. 2 is an exemplary block-flow diagram depicting a process and system for converting a plant material containing cannabinoids into isolated, precipitated cannabinoids (e.g., CBD), in some embodiments employing evaporative crystallization.

The cannabinoid-containing plant material may be selected from *Cannabis sativa, Cannabis indica, Cannabis ruderalis, Echinacea purpurea, Echinacea angustifolia, Acmella oleracea, Helichrysum umbraculigerum,* or *Radula marginata.* In typical embodiments, the cannabinoid-containing plant material is selected from the *Cannabis* genus, including the specific species *Cannabis sativa, Cannabis indica,* and *Cannabis ruderalis.*

The precipitated cannabinoids may be selected from the group consisting of cannabidiol, cannabidiolic acid, cannabinol, cannabigerol, cannabichromene, cannabicyclol, cannabivarin, cannabidivarin, cannabichromevarin, cannabigerovarin, cannabigerol monomethyl ether, cannabielsoin, cannabicitran, tetrahydrocannabinol, tetrahydrocannabinolic acid, tetrahydrocannabiorcol, tetrahydrocannabivarin, tetrahydrocannabiphorol, and combinations thereof.

In some embodiments, the precipitated cannabinoids include cannabidiol. The cannabidiol may at least 50 wt %, or at least 90 wt %, of total cannabinoid compounds contain in the precipitated cannabinoids, for example.

In processes employing evaporative crystallization, the process solvent may be supercritical carbon dioxide. The process solvent may be a non-polar solvent. The process solvent may be a hydrocarbon, such as a $C_2$-$C_8$ alkane. The process solvent may be a $C_1$-$C_{12}$ alcohol, such as ethanol. In some embodiments, the process solvent is not a $C_9$-$C_{11}$ non-aromatic hydrocarbon. In certain embodiments, the process solvent is not a $C_{10}$ alkane. In certain embodiments, the process solvent is not n-decane. In typical embodiments, the process solvent is different than the crystallization-inducing solvent. In certain embodiments, the process solvent is the same compound as the crystallization-inducing solvent, but the process solvent may or may not still be present when the crystallization-inducing solvent is added in step (c). In some embodiments, the crystallization-inducing solvent is or includes n-decane. In some embodiments, the crystallization-inducing solvent is or includes branched decane(s).

In some process embodiments, the process solvent is a hydrocarbon solvent selected from the group consisting of propane, isobutane, n-hexane, cyclohexane, cyclohexene, toluene, xylenes, vegetable oils, and combinations thereof, for example. Dilution gases may be included with the process solvent. For example, inert gases such as Ar or $N_2$ may be present. A pump, such as a centrifugal pump, a positive-displacement pump, an axial-flow pump, etc., may be used to introduce the process solvent in step (b).

In processes employing evaporative crystallization, selection of extraction conditions in step (b) will generally depend on the desired product(s) and choice of process solvent. In some embodiments, the extraction pressure in step (b) is selected from about 1 atm to about 500 atm. In various embodiments, the extraction pressure is about, at least about, or at most about 1, 2, 3, 4, 5, 10, 15, 20, 25, 30, 40, 50, 60, 70, 80, 90, 100, 150, 200, 250, 300, 350, 400, 450, or 500 atm, for example. The extraction time in step (b) may be from about 0.1 minute to about 1 hour, for example. In various embodiments, the extraction time is about, at least about, or at most about 0.1, 0.2, 0.3, 0.4, 0.5, 1, 2, 3, 4, 5, 10, 15, 20, 25, 30, 40, 50, or 60 minutes, for example. The extraction time refers to the amount of time needed for the extraction to take place, once the extraction pressure and temperature are reached. Step (b) may be carried out at an extraction temperature from about 25° C. to about 100° C., for example. In various embodiments, the extraction temperature is about, at least about, or at most about 25° C., 30° C., 40° C., 50° C., 55° C., 60° C., 65° C., 70° C., 80° C., 90° C., or 95° C.

In processes employing evaporative crystallization, in step (b), there may also be generation of residual solids from which the cannabinoids had been extracted. The residual solids generated during the process may be collected from the extraction vessel (step (b)) and may be combusted to generate energy, composted as a soil amendment, utilized as animal feed, or used for other purposes.

In some processes employing evaporative crystallization from a $C_9$-$C_{11}$ non-aromatic hydrocarbon solvent, the first temperature is selected from about 20° C. to about 170° C., such as from about 30° C. to about 100° C. In various embodiments, the first temperature is about, at least about, or at most about 20° C., 25° C., 30° C., 35° C., 40° C., 45° C., 50° C., 60° C., 70° C., 80° C., 90° C., 100° C., 110° C., 120° C., 130° C., 140° C., 150° C., 160° C., or 170° C., including all intervening ranges.

In some processes employing evaporative crystallization from a $C_9$-$C_{11}$ non-aromatic hydrocarbon solvent, the second temperature is selected from about 25° C. to about 250° C., such as from about 100° C. to about 200° C. In various embodiments, the second temperature is about, at least about, or at most about 25° C., 30° C., 40° C., 50° C., 60° C., 70° C., 80° C., 90° C., 100° C., 110° C., 120° C., 130° C., 140° C., 150° C., 160° C., 170° C., 175° C., 180° C., 190° C., or 200° C., including all intervening ranges.

The pressure of evaporative crystallization from a $C_9$-$C_{11}$ non-aromatic hydrocarbon solvent is preferably selected as a function of the specific crystallization-inducing solvent being used. One skilled in the art can select the second temperature for a given solvent and then determine what pressure allows reasonable vaporization to occur (in order to cause precipitation). Alternatively, one skilled in the art can select a desired pressure, such as atmospheric pressure, and then determine what temperature will cause vaporization of the solvent (in to cause precipitation). In various embodiments, the pressure for evaporative crystallization is about, at least about, or at most about 0.01 bar, 0.05 bar, 0.1 bar, 0.5 bar, 0.8 bar, 0.9 bar, 1 bar, 1.1 bar, 1.2 bar, 1.5 bar, 2 bar, 3 bar, 4 bar, or 5 bar, for example. Atmospheric pressure is usually about 1 bar, but this depends on altitude (e.g., the atmospheric pressure in Denver, Colo. is about 0.8 bar).

Isolating in step (e) may utilize one or more of filtration, centrifugation, evaporation, or chromatography. One or more of these steps may be performed to recover the precipitated cannabinoids from the mixture, after the crystallization has occurred or potentially simultaneously with the crystallization—e.g., using apparatus for continuous crystallization and crystal removal via filters or centrifugal forces.

Some variations provide a process for producing cannabinoids from cannabinoid precursors, the process comprising:
(a) providing one or more cannabinoid precursors;
(b) chemically converting the cannabinoid precursors into cannabinoids, thereby forming a cannabinoid-containing solution;
(c) contacting the cannabinoid-containing solution with a crystallization-inducing solvent comprising decane, or another $C_9$-$C_{11}$ non-aromatic hydrocarbon, at a first temperature below the solvent boiling point, to generate a mixture;
(d) vaporizing the crystallization-inducing solvent at a second temperature that is higher than the solvent boiling point at the pressure during this step, to precipitate at least some of the cannabinoids as precipitated cannabinoids; and
(e) isolating and recovering the precipitated cannabinoids from the mixture.

The present invention also provides a product comprising the precipitated cannabinoids produced by a method or a process as disclosed. The product may be packaged, stored, and sold.

The precipitated cannabinoids may be characterized by an average particle size as well as a particle-size distribution. In some embodiments, the precipitated cannabinoids are characterized by an average particle size of about, at least about, or at most about 0.1, 0.2, 0.3, 0.4, 0.5, 1, 1.5, 2, 3, 4, 5, 10, 15, 20, 25, 30, 40, 50, 60, 70, 80, 90, 100, 150, 200, 250, 300, 400, 500 microns, including all intervening ranges, for example. In some embodiments, the precipitated cannabinoids are characterized by a particle size standard deviation of about, or at most about 1%, 10%, 20%, 30%, 40%, 50%, 60%, 70%, 80%, 90%, or 100% of the average (mean) particle size. For example, the precipitated cannabinoid particle size may be 50 μm±10 μm, where 50 μm is the average particle size and 10 μm is the standard deviation σ of the particle size, which equates to 10/50=20% of the average particle size. A narrow particle-size distribution can be beneficial for the final product (e.g., particle size specifications can be critical for formulation and bioavailability of pharmaceuticals). Crystallization from solution, as disclosed herein, is generally capable of producing narrow particle-size distributions.

Particle sizes may be measured by a variety of techniques, including dynamic light scattering, laser diffraction, image analysis, or sieve separation, for example. Dynamic light scattering is a non-invasive, well-established technique for measuring the size and size distribution of particles typically in the submicron region, and with the latest technology down to 1 nanometer. Laser diffraction is a widely used particle-sizing technique for materials ranging from hundreds of nanometers up to several millimeters in size. Exemplary dynamic light scattering instruments and laser diffraction instruments for measuring particle sizes are available from Malvern Instruments Ltd., Worcestershire, UK. Image analysis to estimate particle sizes and distributions can be done directly on photomicrographs, scanning electron micrographs, or other images. Finally, sieving is a conventional technique of separating particles by size.

The present invention also provides a system configured for producing precipitated cannabinoids, the system configured for carrying out a method or a process as disclosed.

Variations provide a system configured for producing cannabinoids from a cannabinoid-containing plant material, the system comprising:
an extraction reactor configured for exposing a starting cannabinoid-containing plant material to a process solvent, thereby forming cannabinoid-containing solution containing cannabinoids dissolved and/or suspended in the process solvent;

a mixer configured for contacting the cannabinoid-containing solution with a crystallization-inducing solvent comprising decane, or another $C_9$-$C_{11}$ non-aromatic hydrocarbon, at a first temperature, to generate a mixture; and a crystallization unit configured for cooling the mixture to reach a second temperature that is lower than the first temperature, to precipitate at least some of the cannabinoids as precipitated cannabinoids, wherein the crystallization unit has an outlet for recovering the precipitated cannabinoids.

Other variations provide a system configured for producing cannabinoids from a cannabinoid-containing plant material, the system comprising:

an extraction reactor configured for exposing a starting cannabinoid-containing plant material to a process solvent, thereby forming cannabinoid-containing solution containing cannabinoids dissolved and/or suspended in the process solvent;

a mixer configured for contacting the cannabinoid-containing solution with a crystallization-inducing solvent comprising decane, or another $C_9$-$C_{11}$ non-aromatic hydrocarbon, at a first temperature, to generate a mixture; and a crystallization unit configured for vaporizing the crystallization-inducing solvent at a second temperature that is higher than the solvent boiling point at the pressure in the crystallization unit, to precipitate at least some of the cannabinoids as precipitated cannabinoids, wherein the crystallization unit has an outlet for recovering the precipitated cannabinoids.

The system may include a subsystem for adjusting temperatures, pressures, residence times, mixing rates, or other conditions within the system. A subsystem may be configured to vary parameters during extraction, mixing, cooling, or heating, such as over a prescribed protocol, or in response to measured variables. For example, an unintended change in crystallization pressure may be compensated by a change in crystallization temperature. As another example, temperature may be maintained constant (isothermal operation) or pressure may be maintained constant (isobaric operation). The subsystem may utilize well-known control logic principles, such as feedback control and feedforward control. Control logic may incorporate results from previous experiments or production campaigns.

In some embodiments, the system further comprises a safety release line that is activated when the pressure within the extraction reactor reaches or exceeds a predetermined pressure, such as a pressure that is higher than the desired extraction pressure within the extraction reactor. Other safety considerations may be applied to the system and methods disclosed herein. The subsystem mentioned above may include protective devices that automatically shut down the operation, when the temperature or pressure exceeds a maximum value. Practical safety-related design may be built into the system as well. Those skilled in the art will understand how to design safe pressure vessels and systems employing them.

It is important to note that a system of the invention is not necessarily a full system intended to start with a cannabinoid-containing plant material (e.g., the system shown in FIG. 1 or FIG. 2). A system may be configured to start with a cannabinoid-containing solution, which may be obtained commercially from a third party, for example (e.g., the system shown in FIG. 3 or FIG. 4). As explained earlier, the cannabinoid-containing solution of FIG. 3 or 4 may contain one or more cannabinoids produced via synthetic pathways.

Figure 3:
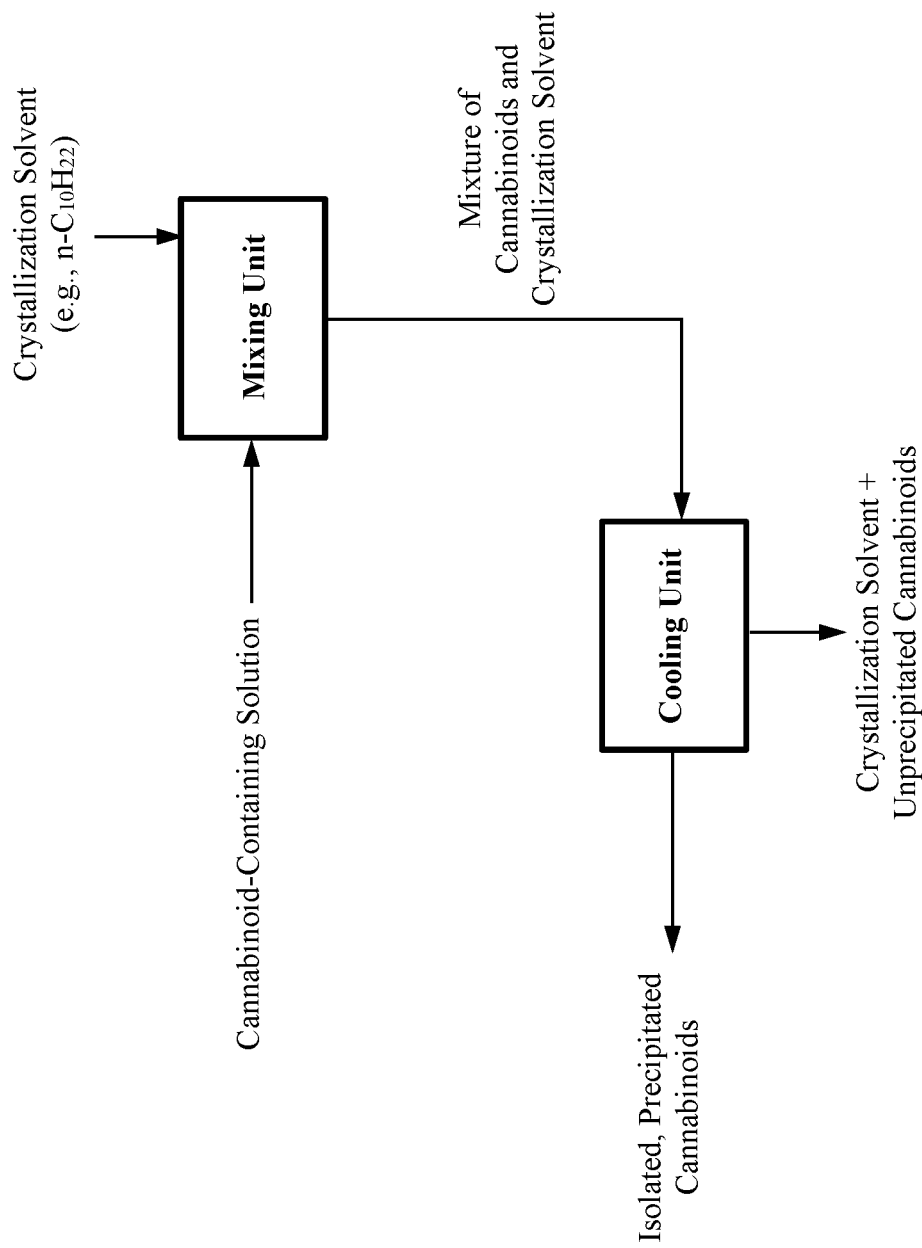
FIG. 3 is an exemplary block-flow diagram depicting a method and system for converting a cannabinoid-containing solution (arbitrary source) into isolated, precipitated cannabinoids (e.g., CBD), in some embodiments employing cooling crystallization.

A system may be configured for isolating one or more cannabinoids from a cannabinoid-containing solution, the system comprising means for contacting the cannabinoid-containing solution with a $C_9$-$C_{11}$ non-aromatic hydrocarbon solvent (e.g., n-decane) at a first temperature, to generate a mixture; means for cooling the mixture to reach a second temperature that is lower than the first temperature, to precipitate at least some of the cannabinoids as precipitated cannabinoids; and means for isolating the precipitated cannabinoids from the mixture. An example of such a system is shown in FIG. 3. FIG. 3 is an exemplary block-flow diagram depicting a method and system for converting a cannabinoid-containing solution (arbitrary source) into isolated, precipitated cannabinoids (e.g., CBD), in some embodiments employing cooling crystallization.

Figure 4:
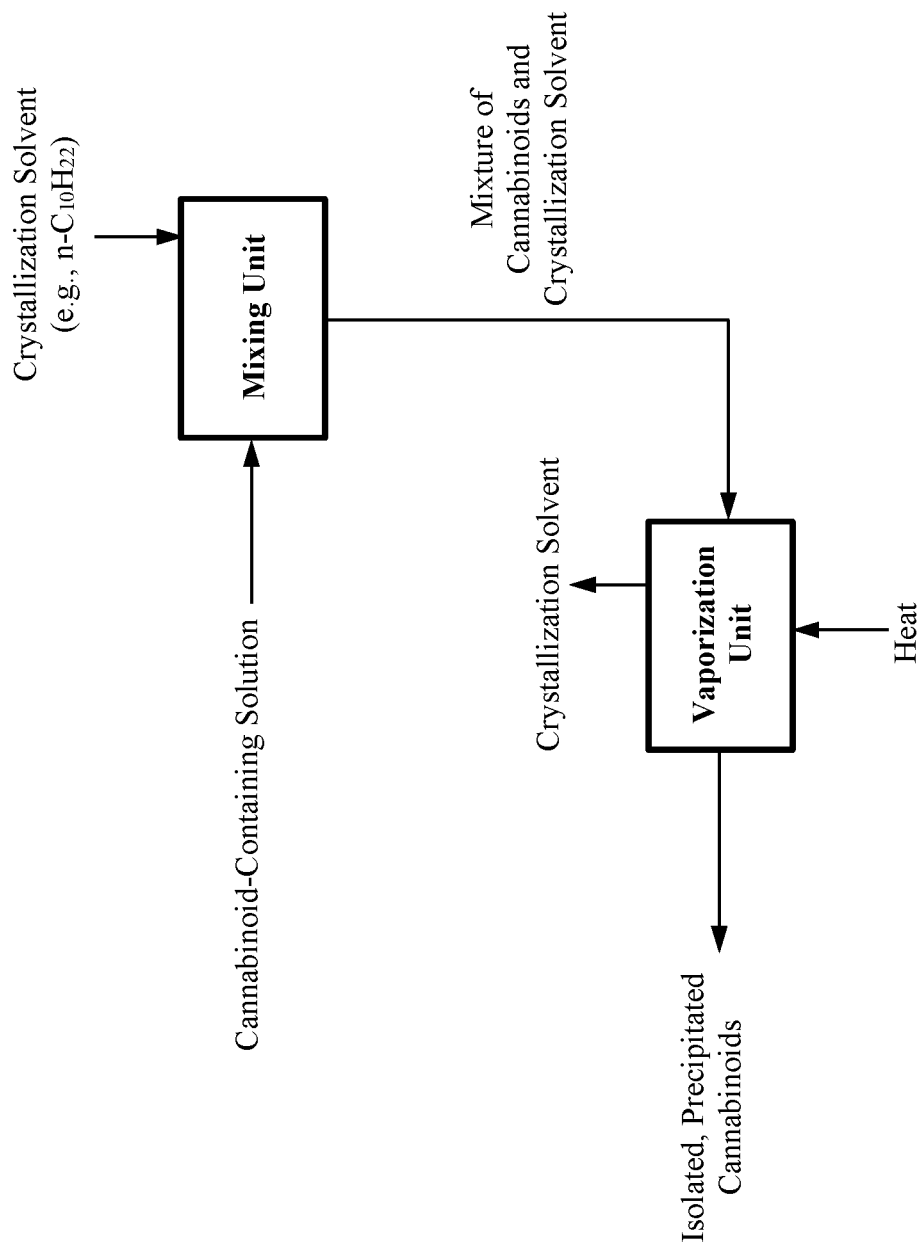
FIG. 4 is an exemplary block-flow diagram depicting a method and system for converting a cannabinoid-containing solution (arbitrary source) into isolated, precipitated cannabinoids (e.g., CBD), in some embodiments employing evaporative crystallization.

In other embodiments employing evaporative crystallization, a system may be configured for isolating one or more cannabinoids from a cannabinoid-containing solution, the system comprising means for contacting the cannabinoid-containing solution with a solvent comprising decane (or another $C_9$-$C_{11}$ non-aromatic hydrocarbon) solvent at a first temperature below the solvent boiling point, to generate a mixture; means for subjecting the mixture to a second temperature that causes vaporization of the solvent, to precipitate at least some of the cannabinoids as precipitated cannabinoids; and means for isolating the precipitated cannabinoids from the mixture. An example of such a system is shown in FIG. 4. FIG. 4 is an exemplary block-flow diagram depicting a method and system for converting a cannabinoid-containing solution (arbitrary source) into isolated, precipitated cannabinoids (e.g., CBD), in some embodiments employing evaporative crystallization.

Any of the systems disclosed herein may be configured to be modular or portable, if desired. A system is preferably designed using automation and process controls, as well as standard safety controls. The throughput of a system may vary widely, from small demo or semi-commercial scale to large commercial scale.

The system may be a batch apparatus, a continuous apparatus, a semi-continuous apparatus, or a combination thereof. The designs disclosed herein can be adapted using known chemical-engineering principles to any scale system for production of large, commercial volumes of products.

The selection of the materials of construction for the system will be dependent on the desired properties and should be considered on a case-by-case basis. Someone skilled in the art of material science or metallurgy will be able to select the appropriate materials for the intended use, based on the information provided in this disclosure.

Other variations of the technology are premised on the isolation of botanical extracts other than cannabinoids. That is, the principles of the invention may be applied to plant materials that do not necessarily contain cannabinoids or cannabinoid precursors, but rather contain another type of botanical material, such as (but by no means limited to) alpha acids, beta acids, herbal extracts, essential oils, flavonoids, alkaloids, and combinations thereof.

Figure 5:
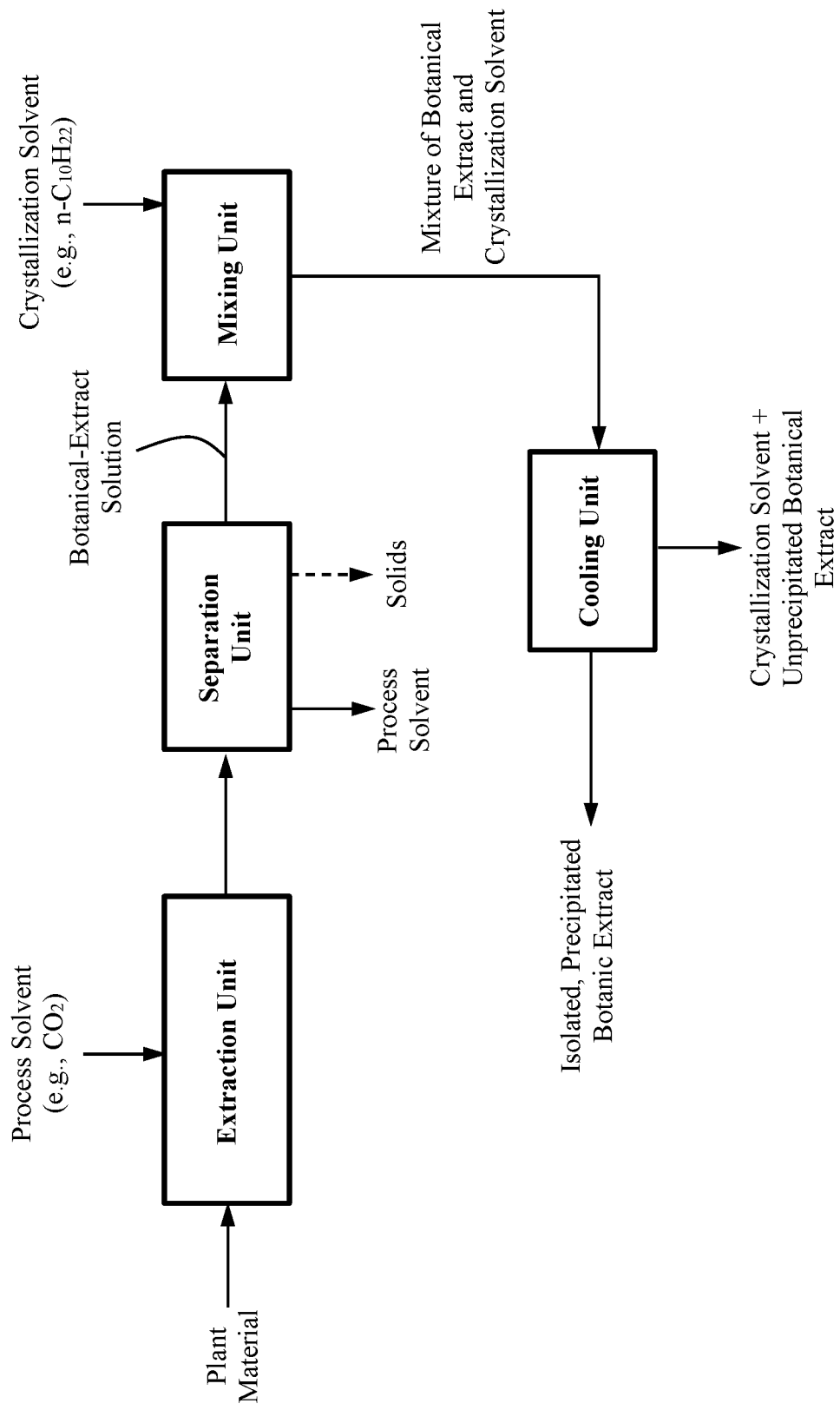
FIG. 5 is an exemplary block-flow diagram depicting a process and system for converting a plant material into an isolated, precipitated botanical extract, in some embodiments employing cooling crystallization.

FIG. 5 is an exemplary block-flow diagram depicting a process and system for converting a plant material into an isolated, precipitated botanical extract, in some embodiments employing cooling crystallization.

Figure 6:
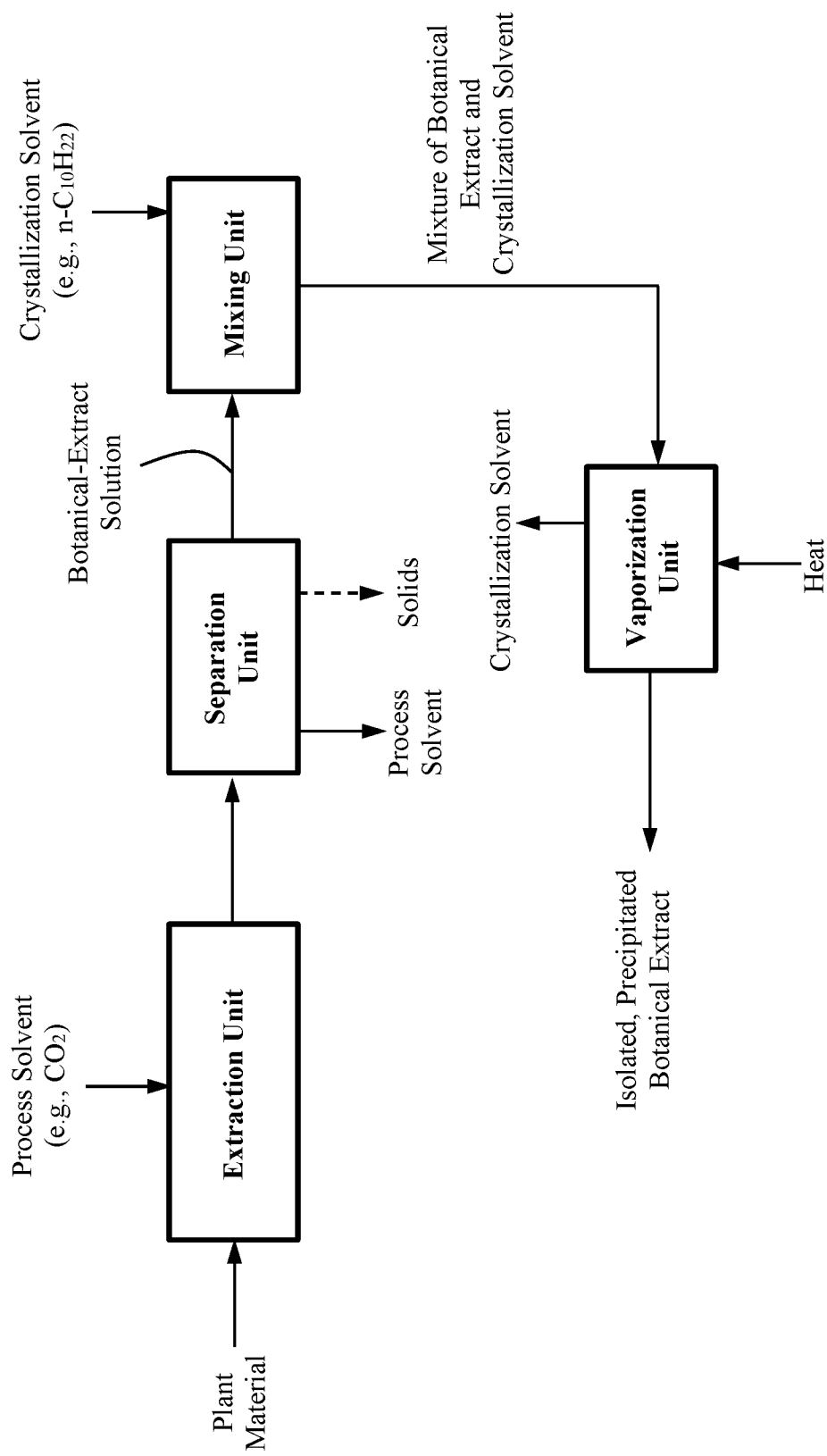
FIG. 6 is an exemplary block-flow diagram depicting a process and system for converting a plant material into an isolated, precipitated botanical extract, in some embodiments employing evaporative crystallization.

FIG. 6 is an exemplary block-flow diagram depicting a process and system for converting a plant material into an isolated, precipitated botanical extract, in some embodiments employing evaporative crystallization.

Figure 7:
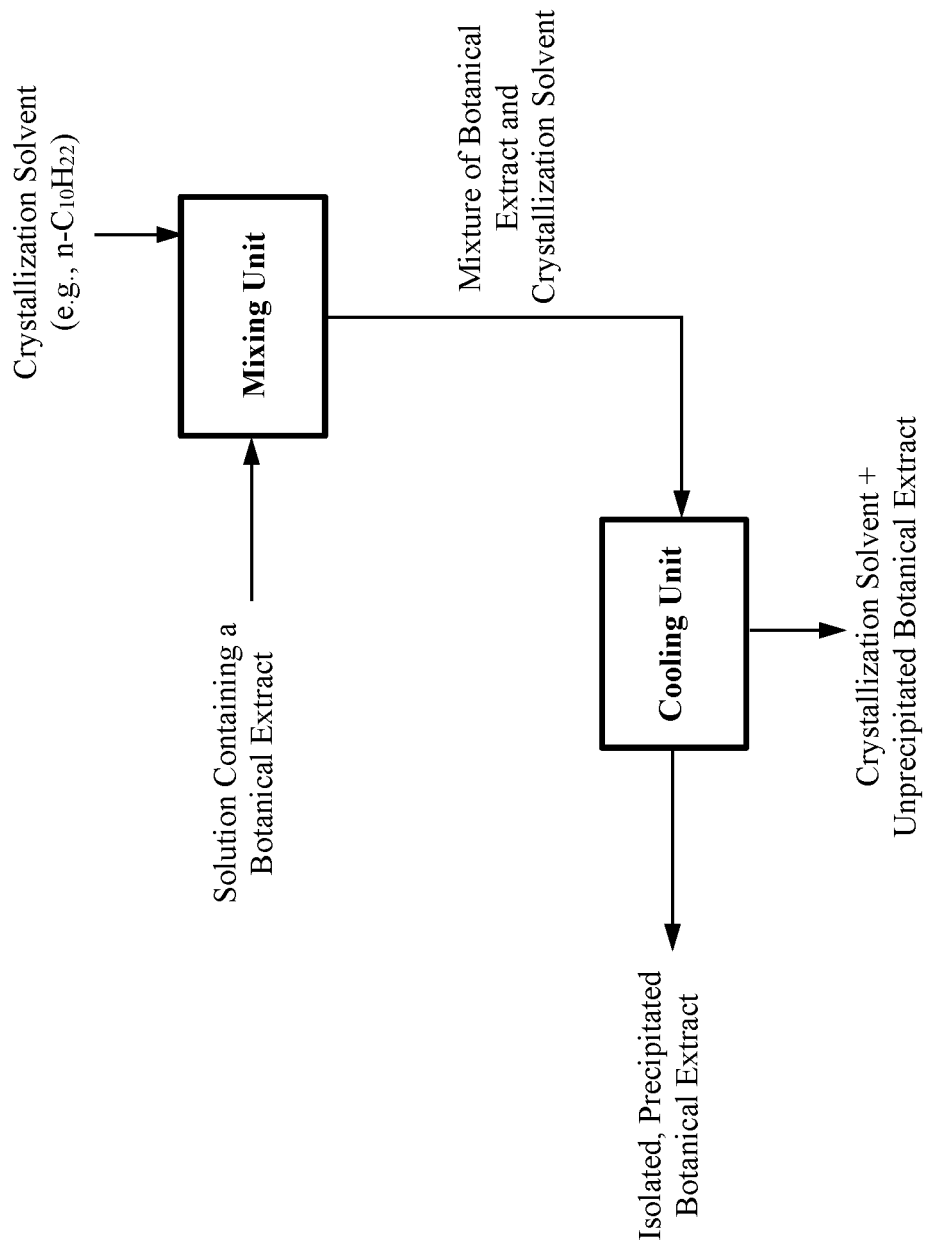
FIG. 7 is an exemplary block-flow diagram depicting a method and system for converting a botanical-extract solution (arbitrary source) into an isolated, precipitated botanical extract, in some embodiments employing cooling crystallization.

FIG. 7 is an exemplary block-flow diagram depicting a method and system for converting a botanical-extract solution (arbitrary source) into an isolated, precipitated botanical extract, in some embodiments employing cooling crystallization.

Figure 8:
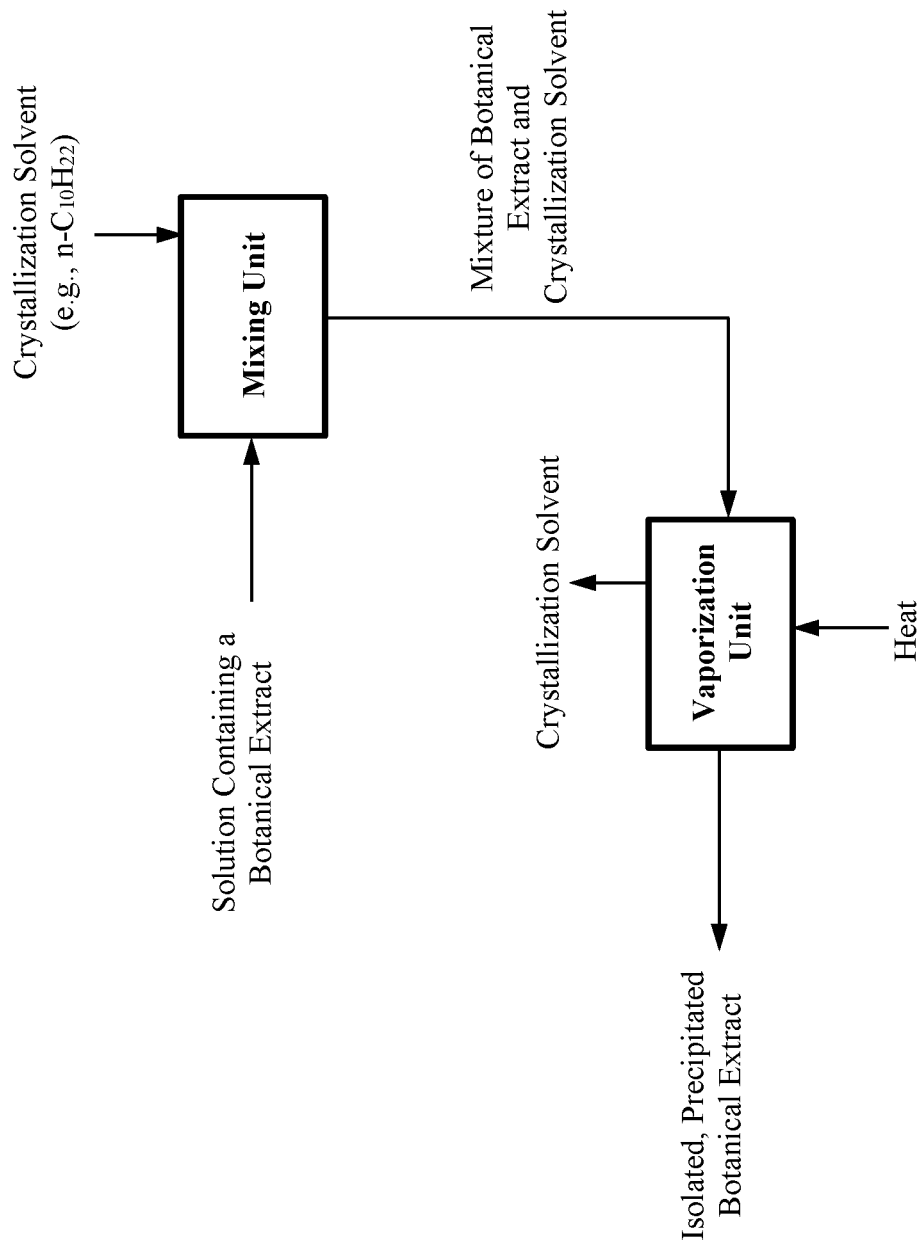
FIG. 8 is an exemplary block-flow diagram depicting a method and system for converting a botanical-extract solution (arbitrary source) into an isolated, precipitated botanical extract, in some embodiments employing evaporative crystallization.

FIG. 8 is an exemplary block-flow diagram depicting a method and system for converting a botanical-extract solution (arbitrary source) into an isolated, precipitated botanical extract, in some embodiments employing evaporative crystallization.

Some variations provide a method of isolating a botanical extract from a solution containing the botanical extract, the method comprising contacting the solution with a $C_9$-$C_{11}$ non-aromatic hydrocarbon solvent at a first temperature, to generate a mixture; cooling the mixture to reach a second temperature that is lower than the first temperature, to precipitate at least some of the botanical extract as a precipitated botanical extract; and isolating the precipitated botanical extract from the mixture.

The $C_9$-$C_{11}$ non-aromatic hydrocarbon solvent may be a $C_{10}$ linear, cyclic, or branched alkane solvent. In certain preferred embodiments, the $C_{10}$ linear, cyclic, or branched alkane solvent is n-decane.

The $C_9$-$C_{11}$ non-aromatic hydrocarbon solvent may be a $C_{10}$ linear, cyclic, or branched alkene solvent or a $C_{10}$ linear, cyclic, or branched alkyne solvent.

The $C_9$-$C_{11}$ non-aromatic hydrocarbon solvent may be a $C_9$ linear, cyclic, or branched alkane solvent or a $C_{11}$ linear, cyclic, or branched alkane solvent.

In some embodiments, the first temperature is selected from about 20° C. to about 170° C. In certain embodiments, the first temperature is selected from about 30° C. to about 100° C. In various embodiments, the first temperature is about, at least about, or at most about 20° C., 30° C., 40° C., 50° C., 60° C., 70° C., 80° C., 90° C., 100° C., 110° C., 120° C., 130° C., 140° C., 150° C., 160° C., or 170° C., including any intervening range.

In some embodiments, the second temperature is selected from about −20° C. to about 150° C., for example. In certain embodiments, the second temperature is selected from about −10° C. to about 100° C., or from about 0° C. to about 50° C. In various embodiments, the second temperature is about, at least about, or at most about −20° C., −10° C., −5° C., 0° C., 5° C., 10° C., 20° C., 30° C., 40° C., 50° C., 60° C., 70° C., 80° C., 90° C., 100° C., 110° C., 120° C., 130° C., 140° C., or 150° C., including any intervening range.

In some embodiments, the temperature difference in degrees Celsius between the first temperature and the second temperature is from about 10° C. to about 200° C. In certain embodiments, the temperature difference is from about 20° C. to about 100° C., such as about, at least about, or at most about 20° C., 30° C., 40° C., 50° C., 60° C., 70° C., 80° C., 90° C., or 100° C., including any intervening range.

The step of isolating the precipitated botanical extract from the mixture may utilize filtration, centrifugation, evaporation, distillation, chromatography, or a combination thereof.

In some embodiments, the botanical extract yield is at least 75%, calculated as mass of the precipitated botanical extract, as a percentage of total mass of the botanical extract in the solution. In certain embodiments, the botanical extract yield is at least 80%, at least 85%, at least 90%, or at least 95%.

In some methods, the solution is obtained from a process of extracting the botanical extract from a plant material, wherein the process is optionally co-located with a site at which the method is conducted. In other embodiments, the solution containing the botanical extract is provided from an external source.

Other variations relating to isolation of botanical extracts provide a method of isolating a botanical extract from a solution containing the botanical extract, the method comprising contacting the solution with a $C_9$-$C_{11}$ non-aromatic hydrocarbon solvent at a first temperature below the solvent boiling point, to generate a mixture; subjecting the mixture to a second temperature that causes vaporization of the solvent, to precipitate at least some of the botanical extract as a precipitated botanical extract; and isolating the precipitated botanical extract from the mixture.

The botanical extract may be selected from the group consisting of alpha acids, beta acids, herbal extracts, essential oils, flavonoids, alkaloids, cannabinoids, and combinations thereof, for example. The botanical extract may be derived from a wide variety of plants or flowers, such as (but by no means limited to) hemp, hops, chamomile, dandelion, *echinacea*, marigold, lavender, aloe, and pine. A large number of botanical extracts is known; see, for example, https://chitosanlab.com/plant-extracts (retrieved on Jun. 30, 2022) for an exemplary listing.

In some embodiments, the $C_9$-$C_{11}$ non-aromatic hydrocarbon solvent is a $C_{10}$ linear, cyclic, or branched alkane solvent, such as (but not limited to) n-decane.

In some embodiments, the $C_9$-$C_{11}$ non-aromatic hydrocarbon solvent is a $C_{10}$ linear, cyclic, or branched alkene solvent or a $C_{10}$ linear, cyclic, or branched alkyne solvent.

In some embodiments, the $C_9$-$C_{11}$ non-aromatic hydrocarbon solvent is a $C_9$ linear, cyclic, or branched alkane solvent.

In some embodiments, the $C_9$-$C_{11}$ non-aromatic hydrocarbon solvent is a $C_{11}$ linear, cyclic, or branched alkane solvent.

In some embodiments, the first temperature is selected from about 20° C. to about 170° C. In certain embodiments, the first temperature is selected from about 30° C. to about 100° C.

In some embodiments, the second temperature is selected from about 25° C. to about 250° C. In certain embodiments, the second temperature is selected from about 100° C. to about 200° C.

The step of isolating the precipitated botanical extract from the mixture may utilize filtration, centrifugation, evaporation, distillation, chromatography, or a combination thereof.

In some methods, the botanical extract yield is at least 75%, calculated as mass of the precipitated botanical extract, as a percentage of total mass of the botanical extract in the solution. The botanical extract yield may be at least 80%, at least 85%, at least 90%, or at least 95%, in various embodiments.

The solution containing the botanical extract may be obtained from a process of extracting the botanical extract from a plant material. That process may be co-located with a site at which the method is conducted. In other embodiments, the solution containing the botanical extract is provided from an external source.

Still other variations provide a process for producing a botanical extract from a plant material, the process comprising:

(a) providing a starting plant material;

(b) exposing the starting plant material to a process solvent, thereby forming a solution containing a botanical extract dissolved and/or suspended in the process solvent;

(c) contacting the solution with a crystallization-inducing solvent comprising a $C_9$-$C_{11}$ non-aromatic hydrocarbon solvent at a first temperature, to generate a mixture;

(d) cooling the mixture to reach a second temperature that is lower than the first temperature, to precipitate at least some of the botanical extract as a precipitated botanical extract; and (e) isolating and recovering the precipitated botanical extract from the mixture.

The botanical extract may be selected from the group consisting of alpha acids, beta acids, herbal extracts, essential oils, flavonoids, alkaloids, cannabinoids, and combinations thereof. Other botanical extracts may be isolated and recovered as well, depending on the starting plant material.

In some processes, the process solvent is supercritical carbon dioxide. In some processes, the process solvent is a non-polar solvent. In certain processes, the process solvent is a hydrocarbon, such as a $C_2$-$C_{12}$ alkane (e.g., a $C_9$-$C_{11}$ alkane, such as n-decane). In some processes, the process solvent is not n-decane. In some processes, the process solvent is a $C_1$-$C_{12}$ alcohol.

Within the crystallization-inducing solvent, the $C_9$-$C_{11}$ non-aromatic hydrocarbon solvent may be a $C_{10}$ linear, cyclic, or branched alkane, such as n-decane, a branched decane, or a combination thereof.

In some processes, the $C_9$-$C_{11}$ non-aromatic hydrocarbon solvent is a $C_{10}$ linear, cyclic, or branched alkene.

In some processes, the $C_9$-$C_{11}$ non-aromatic hydrocarbon solvent is a $C_{10}$ linear, cyclic, or branched alkyne.

In some processes, the $C_9$-$C_{11}$ non-aromatic hydrocarbon solvent is a $C_9$ linear, cyclic, or branched alkane.

In some processes, the $C_9$-$C_{11}$ non-aromatic hydrocarbon solvent is a $C_{11}$ linear, cyclic, or branched alkane.

In some processes, the process solvent is compositionally different than the crystallization-inducing solvent. In other processes, the process solvent is compositionally similar to, or the same as, the crystallization-inducing solvent.

In some processes, the first temperature is selected from about 20° C. to about 170° C., such as from about 30° C. to about 100° C.

In some processes, the second temperature is selected from about −20° C. to about 150° C., such as from about −10° C. to about 100° C., or from about 0° C. to about 50° C.

In some processes, the temperature difference between the first temperature and the second temperature is from about 10° C. to about 200° C., such as from about 20° C. to about 100° C.

Isolating in process step (e) may utilize filtration, centrifugation, evaporation, distillation, chromatography, or a combination thereof.

In some processes, the botanical extract yield is at least 75%, calculated as mass of the precipitated botanical extract, as a percentage of total mass of the botanical extract in the solution. In various processes, the botanical extract yield is at least 80%, at least 85%, at least 90%, or at least 95%.

In some processes, the overall process botanical extract yield is at least 10%, calculated as mass of the botanical extract, as a percentage of total mass of the botanical extract contained in the starting plant material. In various processes, the overall process botanical extract yield is at least 15%, at least 20%, at least 25%, at least 30%, at least 35%, at least 40%, at least 45%, or at least 50%.

The process of isolating and recovering a botanical extract is preferably continuous or semi-continuous. In other embodiments, the process of isolating and recovering a precipitated botanical extract is a batch or semi-batch process.

In some processes of isolating and recovering a botanical extract, all steps may be conducted at a single site. In other embodiments, different process steps are conducted at different site locations.

Variations provide a system configured for producing a botanical extract from a plant material, the system comprising:

an extraction reactor configured for exposing a starting plant material to a process solvent, thereby forming solution containing a botanical extract dissolved and/or suspended in the process solvent;

a mixer configured for contacting the solution with a crystallization-inducing solvent comprising decane, or another $C_9$-$C_{11}$ non-aromatic hydrocarbon, at a first temperature, to generate a mixture; and a crystallization unit configured for cooling the mixture to reach a second temperature that is lower than the first temperature, to precipitate at least some of the a botanical extract as a precipitated a botanical extract, wherein the crystallization unit has an outlet for recovering the precipitated botanical extract.

Other variations provide a system configured for producing a botanical extract from a plant material, the system comprising:

an extraction reactor configured for exposing a starting plant material to a process solvent, thereby forming a solution containing a botanical extract dissolved and/or suspended in the process solvent;

a mixer configured for contacting the solution with a crystallization-inducing solvent comprising decane, or another $C_9$-$C_{11}$ non-aromatic hydrocarbon, at a first temperature, to generate a mixture; and a crystallization unit configured for vaporizing the crystallization-inducing solvent at a second temperature that is higher than the solvent boiling point at the pressure in the crystallization unit, to precipitate at least some of the botanical extract as a precipitated botanical extract, wherein the crystallization unit has an outlet for recovering the precipitated botanical extract.

The system for producing a botanical extract may include a subsystem for adjusting temperatures, pressures, residence times, mixing rates, or other conditions within the system. A subsystem may be configured to vary parameters during extraction, mixing, cooling, or heating, such as over a prescribed protocol, or in response to measured variables. For example, an unintended change in crystallization pressure may be compensated by a change in crystallization temperature. As another example, temperature may be maintained constant (isothermal operation) or pressure may be maintained constant (isobaric operation). The subsystem may utilize well-known control logic principles, such as feedback control and feedforward control. Control logic may incorporate results from previous experiments or production campaigns.

In some embodiments, the system for producing a botanical extract further comprises a safety release line that is activated when the pressure within the extraction reactor reaches or exceeds a predetermined pressure, such as a pressure that is higher than the desired extraction pressure within the extraction reactor. Other safety considerations may be applied to the system. The subsystem may include protective devices that automatically shut down the operation, when the temperature or pressure exceeds a maximum value. Practical safety-related design may be built into the system as well. Those skilled in the art will understand how to design safe pressure vessels and systems employing them.

It is important to note that a system for producing a botanical extract is not necessarily a full system intended to start with a plant material (e.g., the system shown in FIG. 5 or FIG. 6). A system may be configured to start with a solution containing a botanical extract, which may be obtained commercially from a third party, for example (e.g., the system shown in FIG. 7 or FIG. 8).

A system for isolating a botanical extract may be configured for isolating a botanical extract from a solution, the system comprising means for contacting the solution with a $C_9$-$C_{11}$ non-aromatic hydrocarbon solvent (e.g., n-decane) at a first temperature, to generate a mixture; means for cooling the mixture to reach a second temperature that is lower than the first temperature, to precipitate at least some of the botanical extract as a precipitated botanical extract; and means for isolating the precipitated botanical extract from the mixture. An example of such a system is shown in FIG. 7. FIG. 7 is an exemplary block-flow diagram depicting a method and system for converting a botanical extract-containing solution (arbitrary source) into an isolated, precipitated botanical extract, in some embodiments employing cooling crystallization.

In other embodiments employing evaporative crystallization, a system for producing a botanical extract may be configured for isolating a botanical extract from a solution, the system comprising means for contacting the solution with a solvent comprising decane (or another $C_9$-$C_{11}$ non-aromatic hydrocarbon) solvent at a first temperature below the solvent boiling point, to generate a mixture; means for subjecting the mixture to a second temperature that causes vaporization of the solvent, to precipitate at least some of the botanical extract as a precipitated botanical extract; and means for isolating the precipitated botanical extract from the mixture. An example of such a system is shown in FIG. 8. FIG. 8 is an exemplary block-flow diagram depicting a method and system for converting a botanical extract-containing solution (arbitrary source) into an isolated, precipitated botanical extract, in some embodiments employing evaporative crystallization.

The system for producing a botanical extract may be configured to be modular or portable, if desired. A system is preferably designed using automation and process controls, as well as standard safety controls. The throughput of a system may vary widely, from small demo or semi-commercial scale to large commercial scale.

The system for producing a botanical extract may be a batch apparatus, a continuous apparatus, a semi-continuous apparatus, or a combination thereof. The designs disclosed herein can be adapted using known chemical-engineering principles to any scale system for production of large, commercial volumes of products.

The selection of the materials of construction for the system for producing a botanical extract will be dependent on the desired properties and should be considered on a case-by-case basis. Someone skilled in the art of material science or metallurgy will be able to select the appropriate materials for the intended use, based on the information provided in this disclosure.

EXAMPLE

Example 1: CBD Isolation from CBD Distillate Using n-Decane

A starting CBD distillate is obtained with a CBD concentration of 75 wt %. The density of the CBD distillate is 950 kg/m$^3$.

The selected crystallization-inducing solvent for this Example is n-decane. The density of n-decane is 730 kg/m$^3$.

The basis is 1.333 L of CBD distillate. 1.333 L of CBD distillate is heated to 70° C. and mixed with 1 L of n-decane. 1.333 L of CBD distillate weighs 1,266 g. 1.333 L of CBD distillate contains 950 g of CBD. 1 L of n-decane weighs 730 g. The mass ratio of solvent to CBD is 0.77.

The mixture is allowed to passively or actively cool to room temperature, i.e. about 25° C. (for higher effectiveness, the mixture is cooled to about 0° C.). Once cooled to the reduced temperature, the CBD crystals are filtered out and the mother liquor is left behind. This mother liquor contains CBD and all the other cannabinoids that do not crystalize. The mother liquor is analyzed using high-performance liquid chromatography with diode-array detection (Method QSP 1157). The results of the analysis are shown in FIG. 9.

The mass of the mother liquor is the solvent weight plus the non-CBD portion of the distillate with unprecipitated CBD. With the basis above, this works out to 1,132.33 g.

To calculate the amount of CBD that did not precipitate, take 1,132.33 g and multiply it by the concentration of the mother liquor which is about 8.3 wt %. This calculation results in 93.5 g of CBD.

Finally, we can calculate the efficiency of this solvent as $$(1-(93.5 \text{ g}/950 \text{ g}))\times 100 = 90.2\%$$

Comparatively, pentane and n-heptane as crystallization-inducing solvents can only reach a maximum efficiency of 70%, but even to do so the mixture must be cooled severely down to −50° C. Commercially, it is uneconomical to bring down large mixtures to −50° C., which subsequently has a large impact on the bottom line. Surprisingly, it has been discovered that n-decane, as the crystallization-inducing solvent, can produce more efficient results at a much higher temperature compared to other hydrocarbon solvents (e.g., $C_5$-$C_7$ alkanes).

In this detailed description, reference has been made to multiple embodiments and to the accompanying drawings in which are shown by way of illustration specific exemplary embodiments of the invention. These embodiments are described in sufficient detail to enable those skilled in the art to practice the invention, and it is to be understood that modifications to the various disclosed embodiments may be made by a skilled artisan.

Where methods and steps described above indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

All publications, patents, and patent applications cited in this specification are herein incorporated by reference in their entirety as if each publication, patent, or patent application were specifically and individually put forth herein.

The embodiments, variations, and figures described above should provide an indication of the utility and versatility of the present invention. Other embodiments that do not provide all of the features and advantages set forth herein may also be utilized, without departing from the spirit and scope of the present invention. Such modifications and variations are considered to be within the scope of the invention defined by the claims.

What is claimed is:

1. A method of isolating a botanical extract from a solution containing said botanical extract, said method comprising contacting said solution with a $C_9$-$C_{11}$ non-aromatic hydrocarbon solvent at a first temperature, to generate a mixture; cooling said mixture to reach a second temperature that is lower than said first temperature, to precipitate at least some of said botanical extract as a precipitated botanical extract; and isolating said precipitated botanical extract from said mixture.

2. The method of claim 1, wherein said botanical extract is selected from the group consisting of alpha acids, beta acids, herbal extracts, essential oils, flavonoids, alkaloids, cannabinoids, and combinations thereof.

3. The method of claim 1, wherein said $C_9$-$C_{11}$ non-aromatic hydrocarbon solvent is a $C_{10}$ linear, cyclic, or branched alkane solvent.

4. The method of claim 3, wherein said $C_{10}$ linear, cyclic, or branched alkane solvent is n-decane.

5. The method of claim 1, wherein said $C_9$-$C_{11}$ non-aromatic hydrocarbon solvent is a $C_{10}$ linear, cyclic, or branched alkene solvent.

6. The method of claim 1, wherein said $C_9$-$C_{11}$ non-aromatic hydrocarbon solvent is a $C_{10}$ linear, cyclic, or branched alkyne solvent.

7. The method of claim 1, wherein said $C_9$-$C_{11}$ non-aromatic hydrocarbon solvent is a $C_9$ linear, cyclic, or branched alkane solvent.

8. The method of claim 1, wherein said $C_9$-$C_{11}$ non-aromatic hydrocarbon solvent is a $C_{11}$ linear, cyclic, or branched alkane solvent.

9. The method of claim 1, wherein said first temperature is selected from about 20° C. to about 170° C.

10. The method of claim 9, wherein said first temperature is selected from about 30° C. to about 100° C.

11. The method of claim 1, wherein said second temperature is selected from about −20° C. to about 150° C.

12. The method of claim 11, wherein said second temperature is selected from about −10° C. to about 100° C.

13. The method of claim 11, wherein said second temperature is selected from about 0° C. to about 50° C.

14. The method of claim 1, wherein the temperature difference between said first temperature and said second temperature is from about 10° C. to about 200° C.

15. The method of claim 14, wherein said temperature difference is from about 20° C. to about 100° C.

16. The method of claim 1, wherein said isolating utilizes filtration, centrifugation, evaporation, distillation, chromatography, or a combination thereof.

17. The method of claim 1, wherein botanical extract yield is at least 75%, calculated as mass of said precipitated botanical extract, as a percentage of total mass of said botanical extract in said solution.

18. The method of claim 17, wherein said botanical extract yield is at least 80%.

19. The method of claim 17, wherein said botanical extract yield is at least 90%.

20. The method of claim 1, wherein said solution is obtained from a process of extracting said botanical extract from a plant material, and wherein said process is optionally co-located with a site at which said method is conducted.

21. A method of isolating a botanical extract from a solution containing said botanical extract, said method comprising contacting said solution with a $C_9$-$C_{11}$ non-aromatic hydrocarbon solvent at a first temperature below the solvent boiling point, to generate a mixture; subjecting said mixture to a second temperature that causes vaporization of said solvent, to precipitate at least some of said botanical extract as a precipitated botanical extract; and isolating said precipitated botanical extract from said mixture.

22. The method of claim 21, wherein said botanical extract is selected from the group consisting of alpha acids, beta acids, herbal extracts, essential oils, flavonoids, alkaloids, cannabinoids, and combinations thereof.

23. The method of claim 21, wherein said $C_9$-$C_{11}$ non-aromatic hydrocarbon solvent is a $C_{10}$ linear, cyclic, or branched alkane solvent.

24. The method of claim 23, wherein said $C_{10}$ linear, cyclic, or branched alkane solvent is n-decane.

25. The method of claim 21, wherein said $C_9$-$C_{11}$ non-aromatic hydrocarbon solvent is a $C_{10}$ linear, cyclic, or branched alkene solvent.

26. The method of claim 21, wherein said $C_9$-$C_{11}$ non-aromatic hydrocarbon solvent is a $C_{10}$ linear, cyclic, or branched alkyne solvent.

27. The method of claim 21, wherein said $C_9$-$C_{11}$ non-aromatic hydrocarbon solvent is a $C_9$ linear, cyclic, or branched alkane solvent.

28. The method of claim 21, wherein said $C_9$-$C_{11}$ non-aromatic hydrocarbon solvent is a $C_{11}$ linear, cyclic, or branched alkane solvent.

29. The method of claim 21, wherein said first temperature is selected from about 20° C. to about 170° C.

30. The method of claim 29, wherein said first temperature is selected from about 30° C. to about 100° C.

31. The method of claim 21, wherein said second temperature is selected from about 25° C. to about 250° C.

32. The method of claim 31, wherein said second temperature is selected from about 100° C. to about 200° C.

33. The method of claim 21, wherein said isolating utilizes filtration, centrifugation, evaporation, distillation, chromatography, or a combination thereof.

34. The method of claim 21, wherein botanical extract yield is at least 75%, calculated as mass of said precipitated botanical extract, as a percentage of total mass of said botanical extract in said solution.

35. The method of claim 34, wherein said botanical extract yield is at least 80%.

36. The method of claim 34, wherein said botanical extract yield is at least 85%.

37. The method of claim 34, wherein said botanical extract yield is at least 90%.

38. The method of claim 34, wherein said botanical extract yield is at least 95%.

39. The method of claim 21, wherein said solution is obtained from a process of extracting said botanical extract from a plant material.

40. The method of claim 21, wherein said process is co-located with a site at which said method is conducted.

41. A process for producing a botanical extract from a plant material, said process comprising:
   (a) providing a starting plant material;
   (b) exposing said starting plant material to a process solvent, thereby forming a solution containing a botanical extract dissolved and/or suspended in said process solvent;
   (c) contacting said solution with a crystallization-inducing solvent comprising a $C_9$-$C_{11}$ non-aromatic hydrocarbon solvent at a first temperature, to generate a mixture;
   (d) cooling said mixture to reach a second temperature that is lower than said first temperature, to precipitate at least some of said botanical extract as a precipitated botanical extract; and
   (e) isolating and recovering said precipitated botanical extract from said mixture.

42. The process of claim 41, wherein said botanical extract is selected from the group consisting of alpha acids, beta acids, herbal extracts, essential oils, flavonoids, alkaloids, cannabinoids, and combinations thereof.

43. The process of claim 41, wherein said process solvent is supercritical carbon dioxide.

44. The process of claim 41, wherein said process solvent is a non-polar solvent.

45. The process of claim 41, wherein said process solvent is a hydrocarbon.

46. The process of claim 41, wherein said process solvent is a $C_2$-$C_{12}$ alkane.

47. The process of claim 41, wherein said process solvent is a $C_9$-$C_{11}$ alkane.

48. The process of claim 41, wherein said process solvent is n-decane.

49. The process of claim 41, wherein said process solvent is not n-decane.

50. The process of claim 41, wherein said process solvent is a $C_1$-$C_{12}$ alcohol.

51. The process of claim 41, wherein said $C_9$-$C_{11}$ non-aromatic hydrocarbon solvent is a $C_{10}$ linear, cyclic, or branched alkane.

52. The process of claim 51, wherein said $C_{10}$ linear, cyclic, or branched alkane is n-decane.

53. The process of claim 51, wherein said $C_{10}$ linear, cyclic, or branched alkane is a branched decane.

54. The process of claim 41, wherein said $C_9$-$C_{11}$ non-aromatic hydrocarbon solvent is a $C_{10}$ linear, cyclic, or branched alkene.

55. The process of claim 41, wherein said $C_9$-$C_{11}$ non-aromatic hydrocarbon solvent is a $C_{10}$ linear, cyclic, or branched alkyne.

56. The process of claim 41, wherein said $C_9$-$C_{11}$ non-aromatic hydrocarbon solvent is a $C_9$ linear, cyclic, or branched alkane.

57. The process of claim 41, wherein said $C_9$-$C_{11}$ non-aromatic hydrocarbon solvent is a $C_{11}$ linear, cyclic, or branched alkane.

58. The process of claim 41, wherein said process solvent is compositionally different than said crystallization-inducing solvent.

59. The process of claim 41, wherein said first temperature is selected from about 20° C. to about 170° C.

60. The process of claim 59, wherein said first temperature is selected from about 30° C. to about 100° C.

61. The process of claim 41, wherein said second temperature is selected from about −20° C. to about 150° C.

62. The process of claim 61, wherein said second temperature is selected from about −10° C. to about 100° C.

63. The process of claim 61, wherein said second temperature is selected from about 0° C. to about 50° C.

64. The process of claim 41, wherein the temperature difference between said first temperature and said second temperature is from about 10° C. to about 200° C.

65. The process of claim 64, wherein said temperature difference is from about 20° C. to about 100° C.

66. The process of claim 41, wherein said isolating in step (e) utilizes filtration, centrifugation, evaporation, distillation, chromatography, or a combination thereof.

67. The process of claim 41, wherein botanical extract yield is at least 75%, calculated as mass of said precipitated botanical extract, as a percentage of total mass of said botanical extract in said solution.

68. The process of claim 67, wherein said botanical extract yield is at least 85%.

69. The process of claim 41, wherein overall process botanical extract yield is at least 10%, calculated as mass of said botanical extract, as a percentage of total mass of said botanical extract contained in said starting plant material.

70. The process of claim 69, wherein said overall process botanical extract yield is at least 25%.

71. The process of claim 41, wherein said process is continuous or semi-continuous.

72. The process of claim 41, wherein all steps are conducted at a single site.

* * * * *